United States Patent
Kitagawa

(10) Patent No.: US 10,870,824 B2
(45) Date of Patent: Dec. 22, 2020

(54) CELL SUPPORT COMPOSITE AND METHOD FOR PRODUCING CELL SUPPORT COMPOSITE

(71) Applicant: NIKKISO CO., LTD., Tokyo (JP)

(72) Inventor: Fumihiko Kitagawa, Kanazawa Ishikawa (JP)

(73) Assignee: NIKKISO CO., LTD., Tokyo (JP)

( * ) Notice: Subject to any disclaimer, the term of this patent is extended or adjusted under 35 U.S.C. 154(b) by 93 days.

(21) Appl. No.: 15/970,092

(22) Filed: May 3, 2018

(65) Prior Publication Data

US 2018/0245032 A1  Aug. 30, 2018

Related U.S. Application Data

(63) Continuation of application No. PCT/JP2016/081391, filed on Oct. 24, 2016.

(30) Foreign Application Priority Data

Nov. 10, 2015 (JP) .................. 2015-220403

(51) Int. Cl.
| | |
|---|---|
| C12M 1/00 | (2006.01) |
| C07K 14/78 | (2006.01) |
| C12N 5/071 | (2010.01) |
| C12M 1/12 | (2006.01) |
| C12N 5/00 | (2006.01) |
| C07K 14/705 | (2006.01) |

(52) U.S. Cl.
CPC ............. *C12M 25/06* (2013.01); *C07K 14/78* (2013.01); *C12M 25/00* (2013.01); *C12M 25/10* (2013.01); *C12N 5/0068* (2013.01); *C12N 5/0686* (2013.01); *C07K 14/705* (2013.01); *C12N 2533/52* (2013.01)

(58) Field of Classification Search
None
See application file for complete search history.

(56) References Cited

U.S. PATENT DOCUMENTS

2013/0280750 A1  10/2013  Tryggvason et al.

FOREIGN PATENT DOCUMENTS

| EP | 2617811 A1 | 7/2013 |
|---|---|---|
| JP | 2009515558 A | 4/2009 |
| JP | 2010017128 A | 1/2010 |
| JP | 2014501101 A | 1/2014 |
| JP | 2015163052 A | 9/2015 |
| JP | 2015178526 A | 10/2015 |
| WO | WO2008/047760 A1 | 4/2008 |
| WO | WO2011/043130 A1 | 4/2011 |
| WO | WO2015/080297 A1 | 6/2015 |

OTHER PUBLICATIONS

Rahilly et al. "Composition and Organization of Cell-substratum Contacts in Normal and Neoplastic Renal Epithelium", Journal of Pathology, vol. 165, pp. 163-171. (Year: 1991).*
An Office Action in corresponding JP Application No. 2017-550041 dated Apr. 2, 2019 is attached, 5 pages.
Extended Search Report corresponding European Patent Application No. 16863990.4 dated May 22, 2019 is attached, 10 pages.
Sebinger David D R et al: "ECM modulated early kidney development in embryonic organ culture", Biomaterials, Elsevier Science Publishers BV., Barking, GB, vol. 34, No. 28, Jun. 14, 2013, pp. 6670-6682.
Miner J et al: "The laminin alpha chains: expression, developmental transitions, and chromosomal locations of alpha1-5, indentification of heterotrimeric laminins 8-11, and cloning of a novel alpha3 isoform", The Journal of Cell Biology: JCB, The Rockefeller University Press, US, vol. 137, No. 3, May 5, 1997, pp. 685-701.
Fujita Y, et al., "Preparation of Bioartificial Kidney Using Tubular Epithelial Cells, and an Evaluation of Na+ Active Transport and Morphological Changes" *J-GLOBAL*, Feb. 15, 2000, vol. 29, Isssue 1 pp. 172-177.
Mark P. Lewis , et al., Pexicrine effects of basement membrane components on paracrine signaling by renal tubular cells, Kidney International 1996, pp. 48-58, vol. 49.

* cited by examiner

*Primary Examiner* — Michelle F. Paguio Frising
(74) *Attorney, Agent, or Firm* — Muncy, Geissler, Olds & Lowe, P.C.

(57) ABSTRACT

A cell support composite includes: a substrate formed of an artificial material; a laminin molecule or a fragment thereof which adheres to at least a part of the substrate; and a renal tubule epithelial cell or a renal tubule epithelial-like cell which is a culture cell attached to the substrate via the laminin molecule or the fragment thereof.

6 Claims, 17 Drawing Sheets

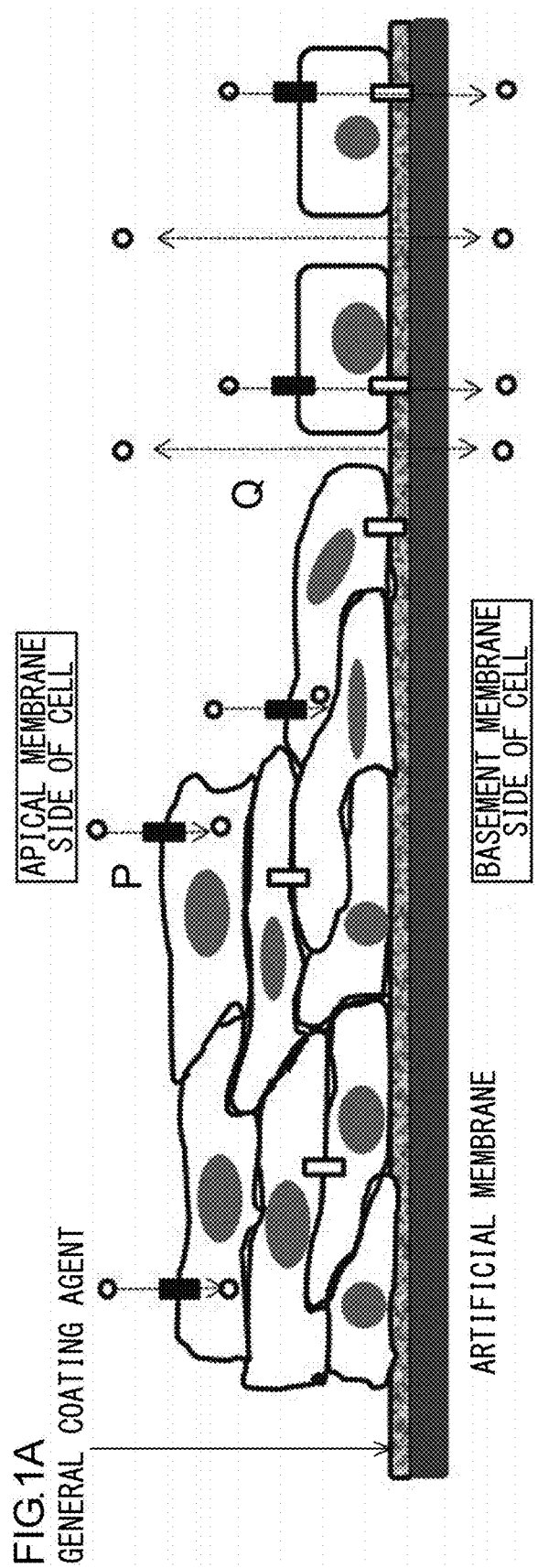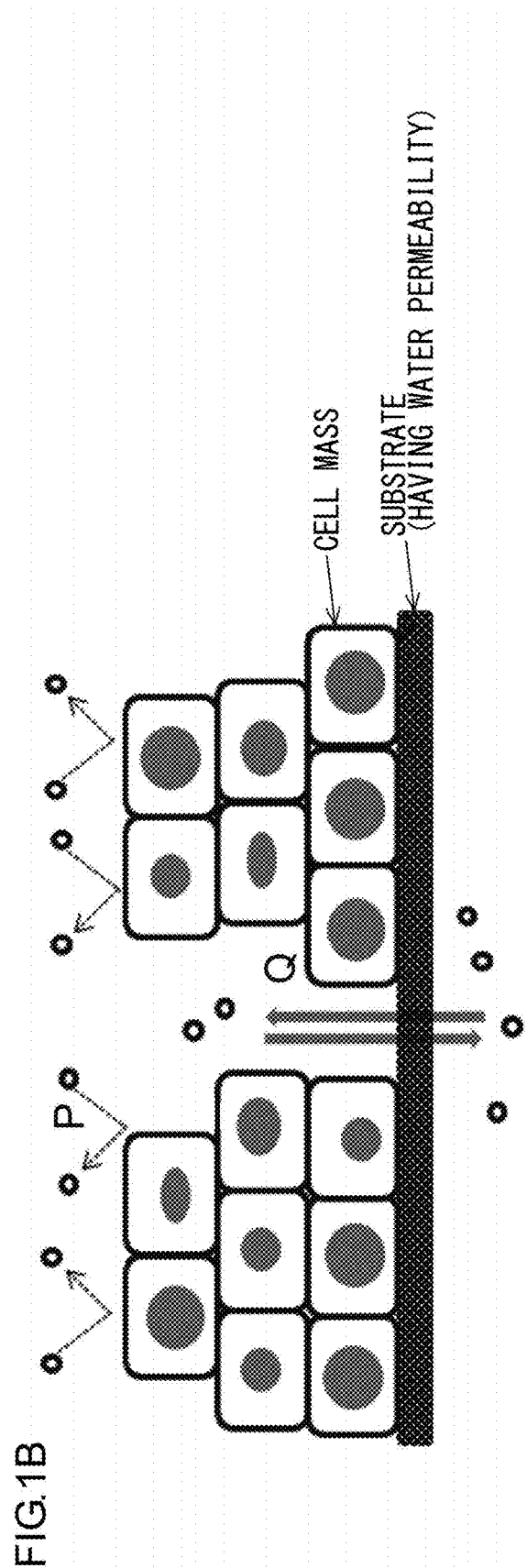

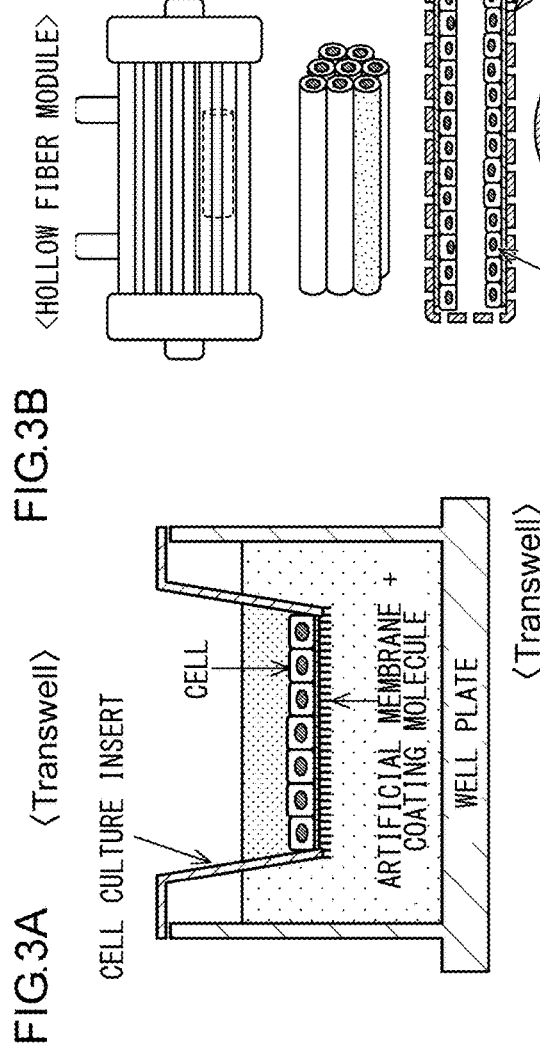
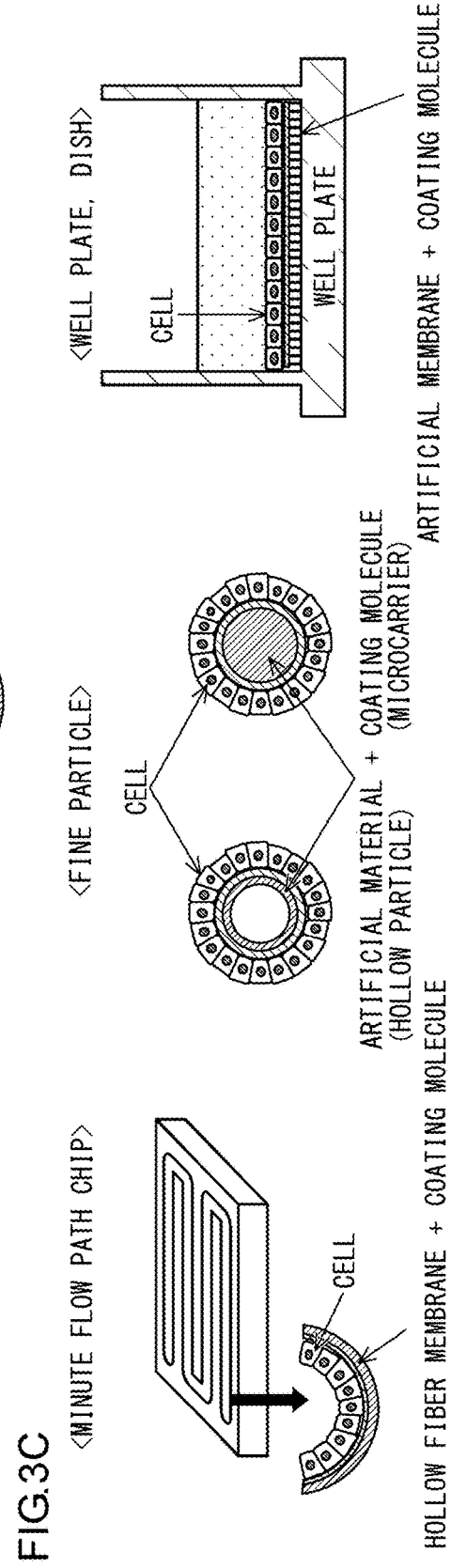
FIG.3A  FIG.3B
FIG.3C

FIG.6A

Synthemax

| CONCENTRA-TION | ADDITION AMOUNT | MAXIMUM ADHESION AMOUNT (AIR DRY) | ADHESION AMOUNT (OVERNIGHT) | DAYS OF CULTURING | | | | | | | |
|---|---|---|---|---|---|---|---|---|---|---|---|
| $\mu g/ml$ | $\mu l/2cm^2$ | $\mu g/cm^2$ | $\mu g/cm^2$ | 5 | 7 | 9 | 12 | 15 | 18 | 24 | 28 |
| 10000 | 300 | 1500.0 | | ○ | ○ | △ | △ | △ | △ | × | × |
| 5000 | 300 | 750.0 | | ○ | ○ | △ | △ | △ | △ | × | × |
| 3000 | 300 | 450.0 | | ○ | ○ | △ | △ | × | × | × | × |
| 2000.0 | 300 | 300.0 | | ○ | △ | △ | × | × | × | × | × |
| 1000.0 | 300 | 150.0 | | ○ | △ | × | × | × | × | × | × |
| 500.0 | 300 | 75.0 | | ○ | △ | × | × | × | × | × | × |
| 100.0 | 300 | 15.0 | | ○ | △ | × | × | × | × | × | × |
| 75.0 | 300 | 11.3 | | ○ | △ | × | × | × | × | × | × |
| 50.0 | 300 | 7.5 | | △ | × | × | × | × | × | × | × |
| 25.0 | 300 | 3.8 | | △ | × | × | × | × | × | × | × |
| 10.0 | 300 | 1.5 | | △ | × | × | × | × | × | × | × |
| 5.0 | 300 | 0.8 | | △ | × | × | × | × | × | × | × |

FIG.6B

Poly-L-Lysine

| CONCENTRA-TION | ADDITION AMOUNT | MAXIMUM ADHESION AMOUNT (AIR DRY) | ADHESION AMOUNT (OVERNIGHT) | DAYS OF CULTURING | | | | | | | |
|---|---|---|---|---|---|---|---|---|---|---|---|
| $\mu g/ml$ | $\mu l/2cm^2$ | $\mu g/cm^2$ | $\mu g/cm^2$ | 5 | 7 | 9 | 12 | 15 | 18 | 24 | 28 |
| 10000 | 300 | 1500.0 | | × | × | × | × | × | × | × | × |
| 5000 | 300 | 750.0 | | × | × | × | × | × | × | × | × |
| 3000 | 300 | 450.0 | | × | × | × | × | × | × | × | × |
| 2000.0 | 300 | 300.0 | | ○ | ○ | △ | × | × | × | × | × |
| 1000.0 | 300 | 150.0 | | ○ | △ | × | × | × | × | × | × |
| 500.0 | 300 | 75.0 | | ○ | △ | × | × | × | × | × | × |
| 100.0 | 300 | 15.0 | | ○ | △ | × | × | × | × | × | × |
| 75.0 | 300 | 11.3 | | ○ | △ | × | × | × | × | × | × |
| 50.0 | 300 | 7.5 | | △ | △ | × | × | × | × | × | × |
| 25.0 | 300 | 3.8 | | △ | △ | × | × | × | × | × | × |
| 10.0 | 300 | 1.5 | | △ | △ | × | × | × | × | × | × |
| 5.0 | 300 | 0.8 | | △ | △ | × | × | × | × | × | × |

FIG.6C

Laminin 111

| CONCENTRA-TION | ADDITION AMOUNT | MAXIMUM ADHESION AMOUNT (AIR DRY) | ADHESION AMOUNT (OVERNIGHT) | DAYS OF CULTURING | | | | | | | |
|---|---|---|---|---|---|---|---|---|---|---|---|
| $\mu g/ml$ | $\mu l/2cm^2$ | $\mu g/cm^2$ | $\mu g/cm^2$ | 5 | 7 | 9 | 12 | 15 | 18 | 24 | 28 |
| 100 | 300 | 15.0 | | ○ | ○ | ○ | ○ | ○ | ○ | ○ | ○ |
| 20 | 300 | 3.0 | | ○ | ○ | ○ | ○ | ○ | ○ | ○ | ○ |
| 10 | 300 | 1.5 | 0.64 | ○ | ○ | ○ | ○ | ○ | ○ | ○ | ○ |
| 8.0 | 300 | 1.2 | | ○ | ○ | ○ | ○ | ○ | ○ | ○ | ○ |
| 6.0 | 300 | 0.9 | | ○ | ○ | ○ | ○ | ○ | ○ | ○ | ○ |
| 5.0 | 300 | 0.8 | | ○ | ○ | ○ | ○ | ○ | ○ | ○ | ○ |
| 4.0 | 300 | 0.6 | 0.19 | ○ | ○ | ○ | ○ | ○ | ○ | ○ | ○ |
| 3.0 | 300 | 0.5 | 0.15 | ○ | ○ | ○ | ○ | ○ | △ | × | × |
| 2.0 | 300 | 0.3 | | ○ | ○ | ○ | △ | △ | × | × | × |
| 1.0 | 300 | 0.2 | | ○ | ○ | △ | × | × | × | × | × |
| 0.5 | 300 | 0.1 | | ○ | △ | × | × | × | × | × | × |
| 0.1 | 300 | 0.0 | | ○ | △ | × | × | × | × | × | × |

FIG.6D

Laminin 211

| CONCENTRA-TION | ADDITION AMOUNT | MAXIMUM ADHESION AMOUNT (AIR DRY) | ADHESION AMOUNT (OVERNIGHT) | DAYS OF CULTURING | | | | | | | |
|---|---|---|---|---|---|---|---|---|---|---|---|
| $\mu g/ml$ | $\mu l/2cm^2$ | $\mu g/cm^2$ | $\mu g/cm^2$ | 5 | 7 | 9 | 12 | 15 | 18 | 24 | 28 |
| 100 | 300 | 15.0 | | ○ | ○ | ○ | ○ | ○ | ○ | ○ | ○ |
| 20 | 300 | 3.0 | | ○ | ○ | ○ | ○ | ○ | ○ | ○ | ○ |
| 10 | 300 | 1.5 | 0.52 | ○ | ○ | ○ | ○ | ○ | ○ | ○ | ○ |
| 8.0 | 300 | 1.2 | 0.45 | ○ | ○ | ○ | △ | △ | △ | △ | △ |
| 6.0 | 300 | 0.9 | | ○ | ○ | △ | × | × | × | × | × |
| 5.0 | 300 | 0.8 | | ○ | △ | × | × | × | × | × | × |
| 4.0 | 300 | 0.6 | | ○ | △ | × | × | × | × | × | × |
| 3.0 | 300 | 0.5 | | ○ | × | × | × | × | × | × | × |
| 2.0 | 300 | 0.3 | | ○ | × | × | × | × | × | × | × |
| 1.0 | 300 | 0.2 | | ○ | × | × | × | × | × | × | × |
| 0.5 | 300 | 0.1 | | ○ | × | × | × | × | × | × | × |
| 0.1 | 300 | 0.0 | | ○ | × | × | × | × | × | × | × |

○ SINGLE LAYER
△ WITH TENDENCY OF AGGREGATION
× FORMATION OF AGGREGATED MASS

FIG.6E

Laminin221

| CONCENTRATION (μg/ml) | ADDITION AMOUNT (μl/2cm²) | MAXIMUM ADHESION AMOUNT (AIR DRY) (μg/cm²) | ADHESION AMOUNT (OVERNIGHT) (μg/cm²) | DAYS OF CULTURING | | | | | | | |
|---|---|---|---|---|---|---|---|---|---|---|---|
| | | | | 5 | 7 | 9 | 12 | 15 | 18 | 24 | 28 |
| 100 | 300 | 15.0 | | ○ | ○ | ○ | ○ | ○ | ○ | ○ | ○ |
| 20 | 300 | 3.0 | | ○ | ○ | ○ | ○ | ○ | ○ | ○ | ○ |
| 10 | 300 | 1.5 | 0.34 | ○ | ○ | ○ | ○ | ○ | ○ | △ | △ |
| 8.0 | 300 | 1.2 | 0.30 | ○ | ○ | ○ | △ | △ | × | × | × |
| 6.0 | 300 | 0.9 | | ○ | ○ | △ | × | × | × | × | × |
| 5.0 | 300 | 0.8 | | ○ | ○ | △ | × | × | × | × | × |
| 4.0 | 300 | 0.6 | | ○ | △ | × | × | × | × | × | × |
| 3.0 | 300 | 0.5 | | ○ | △ | × | × | × | × | × | × |
| 2.0 | 300 | 0.3 | | ○ | △ | × | × | × | × | × | × |
| 1.0 | 300 | 0.2 | | ○ | △ | × | × | × | × | × | × |
| 0.5 | 300 | 0.1 | | ○ | △ | × | × | × | × | × | × |
| 0.1 | 300 | 0.0 | | ○ | △ | × | × | × | × | × | × |

FIG.6F

Laminin311

| CONCENTRATION (μg/ml) | ADDITION AMOUNT (μl/2cm²) | MAXIMUM ADHESION AMOUNT (AIR DRY) (μg/cm²) | ADHESION AMOUNT (OVERNIGHT) (μg/cm²) | DAYS OF CULTURING | | | | | | | |
|---|---|---|---|---|---|---|---|---|---|---|---|
| | | | | 5 | 7 | 9 | 12 | 15 | 18 | 24 | 28 |
| 100 | 300 | 15.0 | | ○ | ○ | ○ | ○ | ○ | ○ | ○ | ○ |
| 20 | 300 | 3.0 | | ○ | ○ | ○ | ○ | ○ | ○ | ○ | ○ |
| 10 | 300 | 1.5 | 0.64 | ○ | ○ | ○ | ○ | ○ | ○ | ○ | ○ |
| 8.0 | 300 | 1.2 | | ○ | ○ | ○ | ○ | ○ | ○ | ○ | ○ |
| 6.0 | 300 | 0.9 | | ○ | ○ | ○ | ○ | ○ | ○ | ○ | ○ |
| 5.0 | 300 | 0.8 | | ○ | ○ | ○ | ○ | ○ | ○ | ○ | ○ |
| 4.0 | 300 | 0.6 | 0.15 | ○ | ○ | ○ | ○ | ○ | ○ | ○ | ○ |
| 3.0 | 300 | 0.5 | | ○ | ○ | ○ | ○ | ○ | ○ | △ | × |
| 2.0 | 300 | 0.3 | 0.07 | ○ | ○ | ○ | △ | △ | × | × | × |
| 1.0 | 300 | 0.2 | | ○ | ○ | △ | × | × | × | × | × |
| 0.5 | 300 | 0.1 | | ○ | △ | × | × | × | × | × | × |
| 0.1 | 300 | 0.0 | | ○ | × | × | × | × | × | × | × |

FIG.6G

Laminin332

| CONCENTRATION (μg/ml) | ADDITION AMOUNT (μl/2cm²) | MAXIMUM ADHESION AMOUNT (AIR DRY) (μg/cm²) | ADHESION AMOUNT (OVERNIGHT) (μg/cm²) | DAYS OF CULTURING | | | | | | | |
|---|---|---|---|---|---|---|---|---|---|---|---|
| | | | | 5 | 7 | 9 | 12 | 15 | 18 | 24 | 28 |
| 100 | 300 | 15.0 | | ○ | ○ | ○ | ○ | ○ | ○ | ○ | × |
| 20 | 300 | 3.0 | | ○ | ○ | ○ | ○ | ○ | ○ | △ | × |
| 10 | 300 | 1.5 | | ○ | ○ | ○ | ○ | ○ | ○ | △ | × |
| 8.0 | 300 | 1.2 | | ○ | ○ | ○ | ○ | ○ | × | △ | × |
| 6.0 | 300 | 0.9 | | ○ | ○ | ○ | ○ | △ | × | × | × |
| 5.0 | 300 | 0.8 | | ○ | ○ | ○ | △ | × | × | × | × |
| 4.0 | 300 | 0.6 | | ○ | △ | △ | × | × | × | × | × |
| 3.0 | 300 | 0.5 | | ○ | △ | △ | × | × | × | × | × |
| 2.0 | 300 | 0.3 | | ○ | △ | × | × | × | × | × | × |
| 1.0 | 300 | 0.2 | | ○ | △ | × | × | × | × | × | × |
| 0.5 | 300 | 0.1 | | ○ | × | × | × | × | × | × | × |
| 0.1 | 300 | 0.0 | | ○ | × | × | × | × | × | × | × |

FIG.6H

Laminin411

| CONCENTRATION (μg/ml) | ADDITION AMOUNT (μl/2cm²) | MAXIMUM ADHESION AMOUNT (AIR DRY) (μg/cm²) | ADHESION AMOUNT (OVERNIGHT) (μg/cm²) | DAYS OF CULTURING | | | | | | | |
|---|---|---|---|---|---|---|---|---|---|---|---|
| | | | | 5 | 7 | 9 | 12 | 15 | 18 | 24 | 28 |
| 100 | 300 | 15.0 | | ○ | ○ | ○ | ○ | △ | × | × | × |
| 20 | 300 | 3.0 | | ○ | ○ | ○ | ○ | △ | × | × | × |
| 10 | 300 | 1.5 | | ○ | ○ | ○ | △ | × | × | × | × |
| 8.0 | 300 | 1.2 | | ○ | ○ | △ | △ | × | × | × | × |
| 6.0 | 300 | 0.9 | | ○ | ○ | △ | △ | × | × | × | × |
| 5.0 | 300 | 0.8 | | ○ | ○ | △ | △ | × | × | × | × |
| 4.0 | 300 | 0.6 | | ○ | ○ | △ | △ | × | × | × | × |
| 3.0 | 300 | 0.5 | | ○ | ○ | △ | △ | × | × | × | × |
| 2.0 | 300 | 0.3 | | ○ | ○ | △ | △ | × | × | × | × |
| 1.0 | 300 | 0.2 | | ○ | ○ | △ | △ | × | × | × | × |
| 0.5 | 300 | 0.1 | | ○ | ○ | △ | △ | × | × | × | × |
| 0.1 | 300 | 0.0 | | ○ | △ | △ | △ | × | × | × | × |

○ SINGLE LAYER
△ WITH TENDENCY OF AGGREGATION
× FORMATION OF AGGREGATED MASS

FIG.6I

Laminin421

| CONCENTRA-TION | ADDITION AMOUNT | MAXIMUM ADHESION AMOUNT (AIR DRY) | ADHESION AMOUNT (OVERNIGHT) | DAYS OF CULTURING | | | | | | | |
|---|---|---|---|---|---|---|---|---|---|---|---|
| μg/ml | μl/2cm² | μg/cm² | μg/cm² | 5 | 7 | 9 | 12 | 15 | 18 | 24 | 28 |
| 100 | 300 | 15.0 |  | ○ | ○ | ○ | ○ | ○ | ○ | ○ | ○ |
| 20 | 300 | 3.0 |  | ○ | ○ | ○ | ○ | ○ | ○ | ○ | ○ |
| 10 | 300 | 1.5 | 0.69 | ○ | ○ | ○ | ○ | ○ | ○ | ○ | ○ |
| 8.0 | 300 | 1.2 |  | ○ | ○ | ○ | ○ | ○ | ○ | △ | △ |
| 6.0 | 300 | 0.9 | 0.54 | ○ | ○ | ○ | ○ | ○ | ○ | △ | △ |
| 5.0 | 300 | 0.8 | 0.50 | ○ | ○ | ○ | ○ | ○ | △ | × | × |
| 4.0 | 300 | 0.6 |  | ○ | ○ | ○ | ○ | △ | × | × | × |
| 3.0 | 300 | 0.5 |  | ○ | ○ | △ | △ | × | × | × | × |
| 2.0 | 300 | 0.3 |  | ○ | △ | △ | △ | × | × | × | × |
| 1.0 | 300 | 0.2 |  | ○ | △ | × | × | × | × | × | × |
| 0.5 | 300 | 0.1 |  | ○ | △ | × | × | × | × | × | × |
| 0.1 | 300 | 0.0 |  | ○ | × | × | × | × | × | × | × |

FIG.6J

Laminin511

| CONCENTRA-TION | ADDITION AMOUNT | MAXIMUM ADHESION AMOUNT (AIR DRY) | ADHESION AMOUNT (OVERNIGHT) | DAYS OF CULTURING | | | | | | | |
|---|---|---|---|---|---|---|---|---|---|---|---|
| μg/ml | μl/2cm² | μg/cm² | μg/cm² | 5 | 7 | 9 | 12 | 15 | 18 | 24 | 28 |
| 100 | 300 | 15.0 |  | ○ | ○ | ○ | ○ | ○ | ○ | ○ | ○ |
| 20 | 300 | 3.0 |  | ○ | ○ | ○ | ○ | ○ | ○ | ○ | ○ |
| 10 | 300 | 1.5 | 0.32 | ○ | ○ | ○ | ○ | ○ | ○ | △ | △ |
| 8.0 | 300 | 1.2 | 0.30 | ○ | ○ | ○ | ○ | △ | △ | × | × |
| 6.0 | 300 | 0.9 |  | ○ | ○ | ○ | ○ | △ | × | × | × |
| 5.0 | 300 | 0.8 |  | ○ | ○ | ○ | △ | × | × | × | × |
| 4.0 | 300 | 0.6 |  | ○ | ○ | ○ | △ | × | × | × | × |
| 3.0 | 300 | 0.5 |  | ○ | ○ | ○ | △ | × | × | × | × |
| 2.0 | 300 | 0.3 |  | ○ | ○ | ○ | △ | × | × | × | × |
| 1.0 | 300 | 0.2 |  | ○ | ○ | △ | △ | × | × | × | × |
| 0.5 | 300 | 0.1 |  | ○ | ○ | × | × | × | × | × | × |
| 0.1 | 300 | 0.0 |  | ○ | △ | × | × | × | × | × | × |

FIG.6K

Laminin521

| CONCENTRA-TION | ADDITION AMOUNT | MAXIMUM ADHESION AMOUNT (AIR DRY) | ADHESION AMOUNT (OVERNIGHT) | DAYS OF CULTURING | | | | | | | |
|---|---|---|---|---|---|---|---|---|---|---|---|
| μg/ml | μl/2cm² | μg/cm² | μg/cm² | 5 | 7 | 9 | 12 | 15 | 18 | 24 | 28 |
| 100 | 300 | 15.0 |  | ○ | ○ | ○ | ○ | ○ | ○ | ○ | ○ |
| 20 | 300 | 3.0 |  | ○ | ○ | ○ | ○ | ○ | ○ | ○ | ○ |
| 10 | 300 | 1.5 | 0.68 | ○ | ○ | ○ | ○ | ○ | ○ | ○ | ○ |
| 8.0 | 300 | 1.2 |  | ○ | ○ | ○ | ○ | ○ | ○ | ○ | ○ |
| 6.0 | 300 | 0.9 |  | ○ | ○ | ○ | ○ | ○ | ○ | ○ | ○ |
| 5.0 | 300 | 0.8 | 0.44 | ○ | ○ | ○ | ○ | ○ | ○ | ○ | ○ |
| 4.0 | 300 | 0.6 |  | ○ | ○ | ○ | △ | △ | △ | △ | × |
| 3.0 | 300 | 0.5 |  | ○ | ○ | △ | × | × | × | × | × |
| 2.0 | 300 | 0.3 |  | ○ | ○ | △ | × | × | × | × | × |
| 1.0 | 300 | 0.2 |  | ○ | △ | × | × | × | × | × | × |
| 0.5 | 300 | 0.1 |  | ○ | △ | × | × | × | × | × | × |
| 0.1 | 300 | 0.0 |  | ○ | △ | × | × | × | × | × | × |

○ SINGLE LAYER
△ WITH TENDENCY OF AGGREGATION
× FORMATION OF AGGREGATED MASS

DRAWING OF Transwell

DRAWING OF NUCLEAR STAINING

DRAWING OF Transwell

Bars: 20μm

FIG.14

| Laminin511-E8 | | | | DAYS OF CULTURING | | | | | | | | |
|---|---|---|---|---|---|---|---|---|---|---|---|---|
| CONCEN-TRATION | ADDITION AMOUNT | MAXIMUM ADHESION AMOUNT (AIR DRY) | ADHESION AMOUNT (OVERNIGHT) | 5 | 7 | 9 | 12 | 15 | 18 | 24 | 28 |
| μg/ml | μl/1.9cm² | μg/cm² | μg/cm² | | | | | | | | |
| 500.00 | 300 | 78.95 | 31.18 | ○ | ○ | ○ | ○ | ○ | ○ | ○ | ○ |
| 100.00 | 300 | 15.79 | | ○ | ○ | ○ | ○ | ○ | ○ | ○ | ○ |
| 50.00 | 300 | 7.89 | 6.21 | ○ | ○ | ○ | ○ | ○ | ○ | ○ | ○ |
| 10.00 | 300 | 1.58 | 1.41 | ○ | ○ | ○ | ○ | ○ | ○ | ○ | ○ |
| 5.00 | 300 | 0.79 | | ○ | ○ | ○ | ○ | ○ | ○ | ○ | ○ |
| 2.50 | 300 | 0.39 | 0.28 | ○ | ○ | ○ | ○ | ○ | ○ | ○ | ○ |
| 1.70 | 300 | 0.27 | 0.2 | ○ | ○ | ○ | ○ | ○ | ○ | ○ | ○ |
| 1.43 | 300 | 0.23 | 0.15 | ○ | ○ | ○ | △ | ○ | ○ | ○ | ○ |
| 1.25 | 300 | 0.20 | 0.09 | ○ | ○ | △ | △ | × | × | × | × |
| 1.00 | 300 | 0.16 | | ○ | △ | × | × | × | × | × | × |
| 0.50 | 300 | 0.08 | | ○ | △ | × | × | × | × | × | × |
| 0.00 | 300 | 0.00 | 0 | ○ | | | | | | | |

CELL SUPPORT COMPOSITE AND METHOD FOR PRODUCING CELL SUPPORT COMPOSITE

CROSS-REFERENCE TO RELATED APPLICATIONS

This application is based upon and claims the benefit of priority from the prior Japanese Patent Application No. 2015-220403, filed on Nov. 10, 2015, and International Patent Application No. PCT/JP2016/081391, filed on Oct. 24, 2016, the entire content of each of which is incorporated herein by reference.

BACKGROUND

Field of the Invention

The present invention relates to a cell support composite, specifically a cell support composite using renal tubule epithelial cells.

Description of the Related Art

In recent years, as a bioartificial kidney that substitutes for the renal functions of patients suffering from acute and chronic renal failures, a module in which a polymer membrane such as a hollow fiber membrane and renal tubule epithelial cells are hybridized is under development. Specifically, when the production, supply and use of a bioartificial kidney are taken into consideration, a bioartificial kidney that can maintain renal functions for several weeks or more is needed.

However, renal tubule epithelial cells that have been separated from a kidney by a treatment with an enzyme cannot maintain their original columnar cell structures, due to disappearance of an in-vivo environment, change in the characteristics of the cells by culturing on a petri dish, and the like. Specifically, it is known that, when renal tubule epithelial cells are seeded on a petri dish or an artificial membrane, the single layer epithelial structures disappear, and thus gaps are generated among the cells and the cells are multilayered. By the occurrence of such phenomena, the function of the bioartificial kidney to absorb again useful components in the blood plasma is deteriorated.

As a technology to avoid the multilayering and inhibition of contact of renal tubule epithelial cells, a bioartificial renal tubule disclosed in Patent Document 1 is known. This technology is such that the contact inhibition and multilayering of renal tubule epithelial cells are suppressed by applying an MEK inhibitor to thereby form a confluent (a state that a container is filled with proliferated cells without gaps) single layer is sustainably formed on an inner surface of an artificial membrane (Patent Document 1).

Patent Document 1: WO2008/047760 A1

However, in the technology of Patent Document 1, it is necessary to seed renal tubule epithelial cells on an artificial membrane, observe the cells under a microscope to confirm that the cells have reached confluent, and then allow the cells to react with an MEK inhibitor. However, many materials for the artificial membrane such as a hollow fiber membrane used in Patent Document 1 are materials that do not allow transmission of light. Furthermore, even in a case where a hollow fiber membrane that can be observed under a microscope is used, since a bioartificial renal tubule has a structure of a module formed by bundled hollow fiber membranes, it is difficult to confirm that the cells have adhered to the inner cavities of the hollow fiber membranes in a confluent state by an observation under a microscope. Therefore, in the technology of Patent Document 1, an MEK inhibitor is administered at a timing that is not the best, while the time when the renal tubule epithelial cell reach confluent on the artificial membrane remains unclear. Therefore, there are cases where the MEK inhibitor is reacted under a state in which gaps are generated among renal tubule epithelial cells, or a state in which cells are multilayered. Consequently, there is a problem that a bioartificial kidney having a high performance cannot be obtained.

SUMMARY OF THE INVENTION

The present invention has been made in view of such problems, and aims at providing a cell support composite in which the stability of a single layer epithelial structure formed by cells has been improved.

To solve the problem, a cell support composite of an aspect of the present invention includes: a substrate formed of an artificial material; a laminin molecule or a fragment thereof which adheres to at least a part of the substrate; and a culture cell attached to the substrate via the laminin molecule or the fragment thereof.

Another aspect of the present invention is a method for producing a cell support composite. This method for producing a cell support composite includes: coating at least a part of a substrate formed of an artificial material with a laminin molecule or a fragment thereof, seeding a culture cell on the laminin molecule or the fragment thereof, and culturing the culture cell to give a single layer structure of the culture cell.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which:

FIGS. 1A and 1B are drawings each schematically showing the constitution of a cell support composite of a conventional art. FIG. 1A is a drawing showing a conventional cell support composite using a general coating agent. FIG. 1B is a drawing showing a conventional cell support composite using no coating agent.

FIG. 2A is a drawing showing the constitution of a cell support composite of an embodiment in which the substrate has water permeability. FIG. 2B is a drawing showing a case where culturing is conducted in a short time in a cell support composite of an embodiment in which the substrate has no water permeability. FIG. 2C is a drawing showing a case where culturing is conducted in a long time in a cell support composite of an embodiment in which the substrate has no water permeability.

FIGS. 3A to 3C are drawings each showing a part of a structure of a device using a cell support composite of an embodiment. FIG. 3A is a drawing showing a part of the structure of a device using a Transwell as a substrate. FIG. 3B is a drawing showing a part of the structure of a dialyzer using a hollow fiber membrane as a substrate. FIG. 3C is a drawing showing a part of a structure of a device using a petri dish, a well plate, a fine flow path, a microcarrier or a hollow fiber membrane as a substrate.

FIGS. 6A to 6D are drawings showing the proliferation states of cells over time in cases where the concentration of an adhesion molecule for coating a petri dish is changed. FIG. 6A is a drawing showing a result of use of Synthemax as a comparative example. FIG. 6B is a drawing showing a result of use of Poly-L-lysine as a comparative example. FIG. 6C is a drawing showing a result of use of Laminin-111 as an example. FIG. 6D is a drawing showing a result of use of Laminin-211 as an example.

FIGS. 6E to 6H are drawings showing the proliferation states of cells over time in cases where the concentration of an adhesion molecule for coating a petri dish is changed. FIG. 6E is a drawing showing a result of use of Laminin-221 as an example. FIG. 6F is a drawing showing a result of use of Laminin-311 as an example. FIG. 6G is a drawing showing a result of use of Laminin-332 as an example. FIG. 6H is a drawing showing a result of use of Laminin-411 as a comparative example.

FIGS. 6I to 6K are drawings showing the proliferation states of cells over time in cases where the concentration of an adhesion molecule for coating a petri dish is changed. FIG. 6I is a drawing showing a result of use of Laminin-421 as an example. FIG. 6J is a drawing showing a result of use of Laminin-511 as an example. FIG. 6K is a drawing showing a result of use of Laminin-521 as an example.

FIG. 11A is a schematic view of a Transwell seen from the side surface. FIG. 11B shows fluorescence microscopic images of nuclear-stained cells in an example using Laminin-521 and a comparative example using gelatin. FIG. 11C shows microscopic images in which the cells are HE-stained regarding the cross-sectional surface of a Transwell.

FIG. 14 is a drawing showing the results of the measurements of the mass of the adhesion molecule and the changes over time of the proliferation state of the cell in cases where the concentration of Laminin-511-E8, which is a fragment of the laminin molecule 30 for coating a petri dish, is changed.

DETAILED DESCRIPTION OF THE INVENTION

Figure 2A:
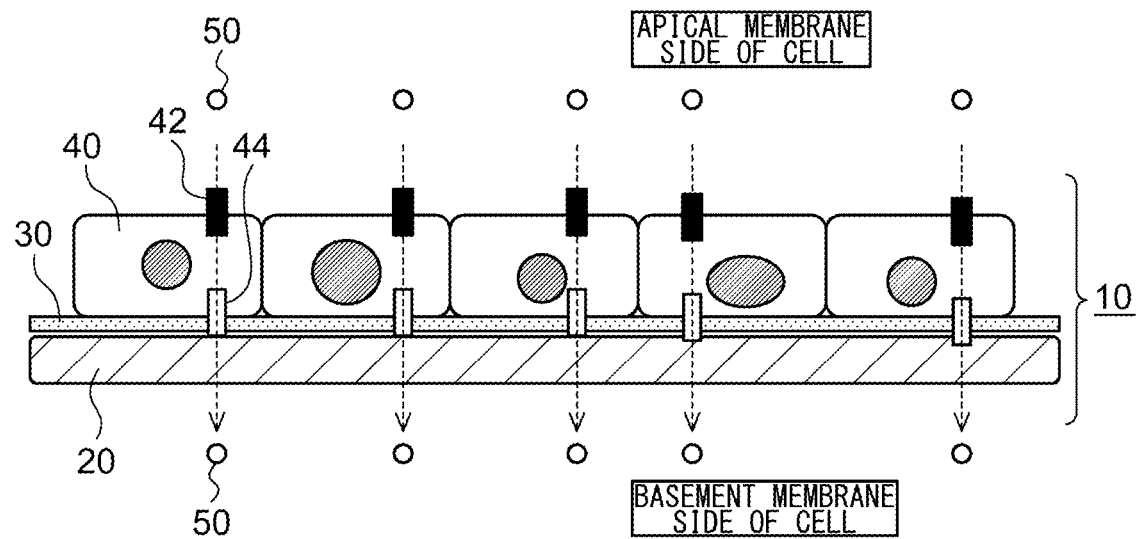
FIGS. 2A to 2C are drawings each schematically showing the constitution of a cell support composite of an embodiment.

A cell support composite of an aspect of the present invention includes: a substrate formed of an artificial material; a laminin molecule or a fragment thereof which adheres to at least a part of the substrate; and a culture cell attached to the substrate via the laminin molecule or the fragment thereof.

According to this aspect, a confluent single layer epithelial structure of culture cells can be formed on a substrate without observation under a microscope. Consequently, a cell support composite having a single layer epithelial structure having improved stability can be provided. Furthermore, formation of pores in the single layer epithelial structure of the cell support composite can be prevented.

Specifically, in a case where a fragment of a laminin molecule is used, there is an advantage that more stable coating can be conducted as compared to a case where a full-length laminin molecule is used, since the fragment of a laminin molecule has a smaller molecular weight than that of the full-length laminin molecule. Furthermore, there is also an advantage that fine regions are easily coated. Furthermore, since aggregation of the laminin molecule hardly occurs, the formation of coating plaques formed during the coating is reduced. By those advantages, inhomogeneity of a cell layer and inhomogeneity of formation of a single layer of cells can be prevented. Furthermore, by using a fragment of a laminin molecule, the laminin molecule can be coated at a high concentration and a high density. In addition, since production efficiency and purification efficiency increase in a recombinant protein at a smaller molecular weight, the yield of the laminin molecule can be increased and the cost can further be decreased.

The culture cells may form a confluent single layer without being substantially multilayered. "Substantially" means that the single layer structure is maintained to the extent that decrease in the transfer efficiency of the substance due to multilayering is not a problem, and does not necessarily mean that multilayering does not occur at all.

The laminin molecule may be selected from one or more of Laminin-111, Laminin-211, Laminin-221, Laminin-311, Laminin-332, Laminin-421, Laminin-511, Laminin-521 or fragments thereof.

The laminin molecule may be selected from one or more of Laminin-311, Laminin-511, Laminin-521 or fragments thereof.

The laminin molecule or the fragment thereof may be selected from any one of a recombinant of Laminin-311 that adheres to the substrate at an amount of 0.07 µg/cm$^2$ or more, a recombinant of Laminin-511 that adheres to the substrate at an amount of 0.05 µg/cm$^2$ or more, a variant of E8 region of Laminin-511 that adheres to the substrate at an amount of 0.15 µg/cm$^2$ or more, a recombinant of Laminin-521 that adheres to the substrate at an amount of 0.33 µg/cm$^2$ or more, or fragments thereof. In the specification of the present application, a recombinant refers to a protein obtained from a recombinant gene obtained by utilizing gene recombination. A variant refers to a protein obtained by further modifying a gene from which the recombinant is derived. The variant comprises a protein in which mutation is introduced in a recombinant, a partial protein of a recombinant, and a protein having a peptide derived from a recombinant.

Another aspect of the present invention is a method for producing a cell support composite. This method for producing a cell support composite includes: coating at least a part of a substrate formed of an artificial material with a laminin molecule or a fragment thereof, seeding a culture cell on the laminin molecule or the fragment thereof, and culturing the culture cell to give a single layer structure of the culture cell.

According to this aspect, a confluent single layer epithelial structure of culture cells can be formed on a substrate without observation under a microscope. Consequently, a cell support composite having a single layer epithelial structure with improved stability can be provided. Furthermore, formation of pores in the single layer epithelial structure of the cell support composite can be prevented.

In this method for producing a cell support composite, the laminin molecule may be selected from one or more of Laminin-111, Laminin-211, Laminin-221, Laminin-311, Laminin-332, Laminin-421, Laminin-511, Laminin-521 or fragments thereof.

In this method for producing a cell support composite, the laminin molecule may be selected from one or more of Laminin-311, Laminin-511, Laminin-521 or a fragment thereof.

The coating with the laminin molecule or the fragment thereof may include any one of: coating with Laminin-311 at a concentration of 2.0 µg/ml or more to give an adhesion amount of 0.07 µg/cm$^2$ or more; coating with Laminin-511 at a concentration of 2.0 µg/ml or more to give an adhesion amount of 0.05 µg/cm$^2$ or more; coating with a variant of E8 region of Laminin-511 at a concentration of 1.4 µg/ml or more to give an adhesion amount of 0.15 µg/cm$^2$ or more; and coating with Laminin-521 at a concentration of 4.0 µg/ml or more to give an adhesion amount of 0.33 µg/cm$^2$ or more.

The embodiments for carrying out the present invention will be explained below in detail with referring to the drawings. In the explanation, an identical symbol is added to elements that are identical, and overlapping explanations are suitably omitted.

FIGS. 1A and 1B are drawings that schematically show the constitution of a cell support composite of a conventional art. FIG. 1A is a drawing showing a conventional cell support composite using a general coating agent. FIG. 1B a drawing showing a conventional cell support composite using no coating agent. For example, as shown in FIG. 1, in a conventional cell support composite using renal tubule epithelial cells and a general coating agent, the renal tubule epithelial cell are multilayered, or conversely, gaps are formed among the cells. Consequently, in a multilayering region, there was a problem that the transfer of a useful substance from the membrane at the side of the apical membrane of the cell to the side of the basement membrane of the cell via a transporter is not conducted in an efficient manner (arrow P). On the other hand, there was a problem that the transfer of the substance from the gaps formed among the cells in a concentration-dependent manner occurs via the artificial membrane (arrow Q). In this point, there was a similar problem in the conventional cell support composite using no coating agent shown in FIG. 1B.

Embodiments

Figure 2B:
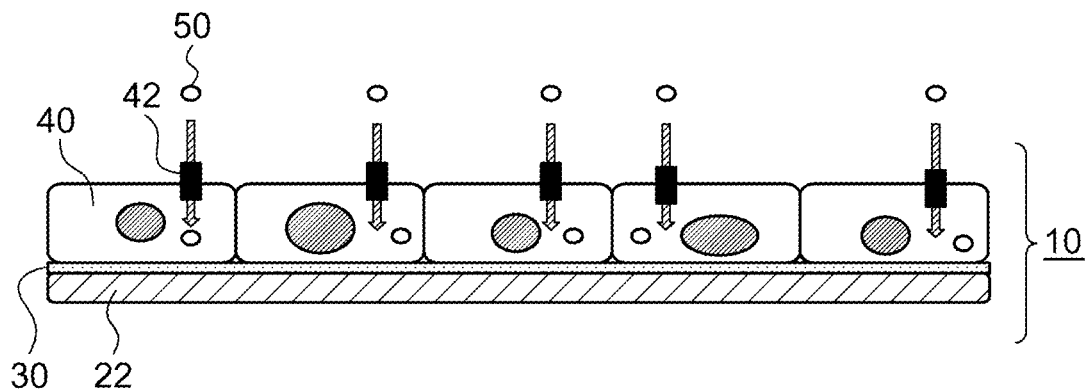
Figure 2C:
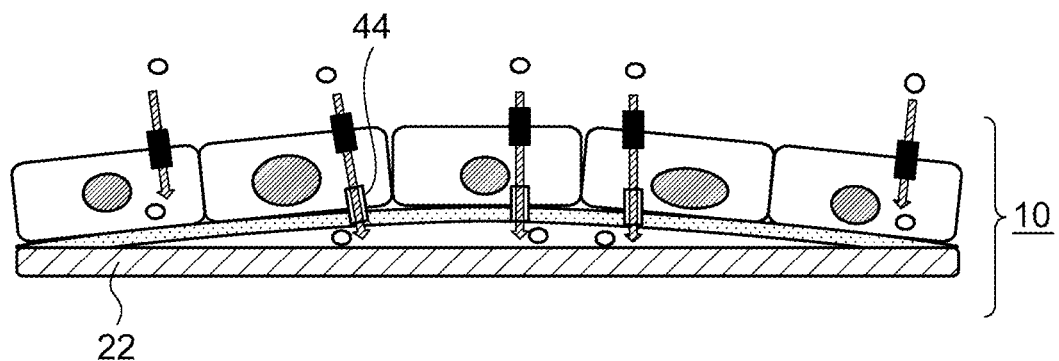

FIGS. 2A to 2C are drawings that schematically show the constitution of a cell support composite 10 of an embodiment. FIG. 2A is a drawing showing the constitution of the cell support composite of an embodiment in which the substrate has water permeability. FIG. 2B is a drawing showing a case where culturing is conducted for a short time in the cell support composite of an embodiment in which the substrate has no water permeability. FIG. 2C is a drawing showing a case where culturing is conducted for a long time in the cell support composite of an embodiment in which the substrate has no water permeability.

As shown in FIG. 2A, the cell support composite 10 has a substrate 20, which is formed of an artificial material, a laminin molecule 30 or a fragment thereof, which is an adhesion molecule that adheres to at least a part of the substrate, and culture cells 40 adhering to the substrate 20 via the laminin molecule 30 or the fragment thereof. "At least a part of the substrate 20" herein refers to, for example, "at least one surface of the substrate 20 having a plane surface or a curved surface". In a case where the substrate 20 has a flat plate-like structure, the surface refers to at least one surface thereof. In a case where the substrate 20 has a cylindrical structure, the surface refers to at least one of the inner surface or outer surface thereof. It is preferable that the culture cells form a confluent single layer without being substantially multilayered.

Substrate 20

The substrate 20 is a module used for culturing renal tubule epithelial cells. FIG. 2A shows a case where the substrate 20 has permeability to water and various ions. In this case, it is preferable that the substrate 20 also has permeability to sugars and low molecular weight proteins. For this purpose, pores are formed in the substrate 20. The substrate 20 has an average pore size of 5 µm or less. As such substrate 20, for example, a Transwell (Corning Inc.: average pore size: 0.4 or 3.0 µm) can be used. In a case where the average pore size is greater than 5 µm, it is not preferable since the cells may pass through the substrate 20.

The shape of the substrate 20 is not specifically limited, and preferable examples include artificial membranes such as hollow fiber membranes, Transwell and planar membranes, fine flow path chips, solid particles and hollow particles. Examples of these are mentioned below by using FIGS. 3A to 3C. As shown in FIGS. 2B and 2C, when the kind and concentration of the adhesion molecule are considered and the amount of a drug that has been ingested by a culture cell 40 are evaluated, it is not necessary that the substrate always has water permeability. In this case, a petri dish, a well plate or the like having no water permeability as the substrate 20 may be coated with the laminin molecule 30 or the fragment thereof, and the culture cell 40 may be cultured on the coated substrate 20. In a case where the cell is cultured for a short time, the culture cell 40 ingests a useful substance 50 therein (FIG. 2B). On the other hand, in a case where the cell is cultured for a long time, a phenomenon that the cell layer is lifted by the release of the ingested useful substance 50 from a transporter 44 at the side of the cell basement membrane and a dome is formed can be observed (FIG. 2C).

The material of the substrate 20 is not specifically limited, and is preferably, for example, a polystyrene, a polycarbonate (PC), a polyester (PET), a polyester-based polymer alloy (PEPA), an ethylene-vinyl alcohol copolymer (EVOH), a polyethylene, a polysulfone (PSf) or a polyethersulfone (PES).

Laminin Molecule 30

The laminin molecule 30 is an adhesion molecule by which at least a part of the substrate is coated, and has a heterotrimer structure having one α-chain, one β-chain and one γ-chain, respectively. Currently 5 kinds of α-chains, 3 kinds of β-chains and 3 kinds of γ-chains have been identified. It is known that the laminin molecule 30 forms at least 12 kinds of isofoams by combinations of these chains. In this embodiment, one or more of Laminin-211, Laminin-221, Laminin-311, Laminin-332, Laminin-421, Laminin-511 and Laminin-521, or fragments thereof, which have not been conventionally used in cell support composites are used. The laminin molecule 30 in this embodiment also includes modified laminins in which predetermined modifying group(s) is/are attached to one or more sites of the above-mentioned isofoams.

Among the isofoams of laminins, Laminin-311, Laminin-511 and Laminin-521 are more preferable since they have a higher electrical resistance values, which are indices of a barrier function among cells, than that of Laminin-111. Furthermore, Laminin-511 and Laminin-521 are more preferable since their costs are less expensive than that of Laminin-111.

The concentration of the laminin molecule 30 is suitably adjusted so that the cell support composite 10 can maintain performances over practical duration. Furthermore, such duration is preferably 2 weeks or more, more preferably 3 weeks or more, the most preferably 4 weeks or more from the initiation of the culturing. The concentration of the laminin molecule 30 will be mentioned below in the production method.

For the measurement of the amount of the laminin molecule 30 adhered to the cell support composite 10, a method known to persons skilled in the art can be used. The adhesion molecular amount after coating by allowing a coating solution containing the laminin molecule 30 to stand still at 4° C. overnight is quantified by using, for example, a 2-D Quant Kit (GE Healthcare). Alternatively, an adhesion amount after air drying can be quantified.

In a case of Laminin-111, it is preferable to conduct coating at a concentration of 3.0 µg/ml or more to give an adhesion amount of about 0.15 µg/cm$^2$ or more. By this way, a single layer structure of the culture cells can be maintained for about 15 days or more. It is further preferable to conduct coating at a concentration of 4.0 µg/ml or more to give an adhesion amount of about 0.19 µg/cm$^2$ or more. By this way, a single layer structure of the culture cells can be maintained for 28 days or more. This is because when the concentration of Laminin-111 is lower than 3.0 µg/ml, there is a possibility that functions as an adhesion molecule cannot be sufficiently exerted. Furthermore, when the concentration of commercially available Laminin-111 is taken into consideration, since the treatment becomes complex and the cost increases at a concentration greater than 100 µg/ml, the concentration is preferably 100 µg/ml or less.

In a case of Laminin-211, it is preferable to conduct coating at a concentration of greater than 8.0 µg/ml to give an adhesion amount of greater than about 0.45 µg/cm$^2$. By this way, a single layer structure of the culture cells can be maintained for about 15 days or more. It is further preferable to conduct coating at a concentration of 10 µg/ml or more to give an adhesion amount of about 0.52 µg/cm$^2$ or more. By this way, a single layer structure of the culture cells can be maintained for 28 days or more. This is because when the concentration of Laminin-211 is 8.0 µg/ml or less, there is a possibility that functions as an adhesion molecule cannot be sufficiently exerted. Furthermore, when the concentration of commercially available Laminin-211 is taken into consideration, since the treatment becomes complex and the cost increases at a concentration greater than 100 µg/ml, the concentration is preferably 100 µg/ml or less.

In a case of Laminin-221, it is preferable to conduct coating at a concentration of greater than 8.0 µg/ml to give an adhesion amount of greater than about 0.30 µg/cm$^2$. By this way, a single layer structure of the culture cells can be maintained for about 15 days or more. It is further preferable to conduct coating at a concentration of 10 µg/ml or more to give an adhesion amount of about 0.34 µg/cm$^2$ or more. By this way, a single layer structure of the culture cells can be maintained for 18 days or more. This is because when the concentration of Laminin-221 is 8.0 µg/ml or less, there is a possibility that functions as an adhesion molecule cannot be sufficiently exerted. Furthermore, when the concentration of commercially available Laminin-221 is taken into consideration, since the treatment becomes complex and the cost increases at a concentration greater than 100 µg/ml, the concentration is preferably 100 µg/ml or less.

In a case of Laminin-311, it is preferable to conduct coating at a concentration of about 2.5 µg/ml or more to give an adhesion amount of about 0.10 µg/cm$^2$ or more. By this way, a single layer structure of the culture cells can be maintained for about 15 days or more. It is further preferable to conduct coating at a concentration of 4.0 µg/ml or more to give an adhesion amount of about 0.15 µg/cm$^2$ or more. By this way, a single layer structure of the culture cells can be maintained for 28 days or more. This is because when the concentration of Laminin-311 is lower than about 2.5 µg/ml, there is a possibility that functions as an adhesion molecule cannot be sufficiently exerted. Furthermore, when the concentration of commercially available Laminin-311 is taken into consideration, since the treatment becomes complex and the cost increases at a concentration greater than 100 µg/ml, the concentration is preferably 100 µg/ml or less.

In a case of Laminin-332, it is preferable to conduct coating at a concentration of 8.0 µg/ml or more. By this way, a single layer structure of the culture cells can be maintained for 15 days or more. It is further preferable to conduct coating at a concentration of 10 µg/ml or more. By this way, a single layer structure of the culture cells can be maintained for 18 days or more. This is because when the concentration of Laminin-332 is lower than about 8.0 µg/ml, there is a possibility that functions as an adhesion molecule cannot be sufficiently exerted. Furthermore, when the concentration of commercially available Laminin-332 is taken into consideration, since the treatment becomes complex and the cost increases at a concentration greater than 100 µg/ml, the concentration is preferably 100 µg/ml or less.

In a case of Laminin-421, it is preferable to conduct coating at a concentration of 5.0 µg/ml or more to give an adhesion amount of about 0.50 µg/cm$^2$ or more. By this way, a single layer structure of the culture cells can be maintained for 15 days or more. It is more preferable to conduct coating at a concentration of 6.0 µg/ml or more to give an adhesion amount of about 0.54 µg/cm$^2$ or more. By this way, a single layer structure of the culture cells can be maintained for 18 days or more. It is further preferable to conduct coating at a concentration of 10 µg/ml or more to give an adhesion amount of about 0.69 µg/cm$^2$ or more. By this way, a single layer structure of the culture cells can be maintained for 28 days or more. This is because when the concentration of Laminin-421 is lower than about 5.0 µg/ml, functions as an adhesion molecule cannot be sufficiently exerted. Furthermore, when the concentration of commercially available Laminin-421 is taken into consideration, since the treatment becomes complex and the cost increases at a concentration greater than 100 µg/ml, the concentration is preferably 100 µg/ml or less.

In a case of Laminin-511, it is preferable to conduct coating at a concentration of greater than about 8.0 µg/ml to give an adhesion amount of greater than about 0.30 µg/cm$^2$. By this way, a single layer structure of the culture cells can be maintained for about 15 days or more. It is more preferable to conduct coating at a concentration of 10 µg/ml or more to give an adhesion amount of about 0.32 µg/cm$^2$ or more. By this way, a single layer structure of the culture cells can be maintained for 18 days or more. This is because when the concentration of Laminin-511 is about 8.0 µg/ml or less, there is a possibility that functions as an adhesion molecule cannot be sufficiently exerted. Furthermore, when the concentration of commercially available Laminin-511 is taken into consideration, since the treatment becomes complex and the cost increases at a concentration greater than 100 µg/ml, the concentration is preferably 100 µg/ml or less.

In a case of Laminin-521, it is preferable to conduct coating at a concentration of about 4.5 µg/ml or more to give an adhesion amount of about 0.40 µg/cm$^2$ or more. By this way, a single layer structure of the culture cells can be maintained for about 15 days or more. It is further preferable to conduct coating at a concentration of 5.0 µg/ml or more to give an adhesion amount of 0.44 µg/cm$^2$ or more. By this way, a single layer structure of the culture cells can be maintained for 28 days or more. This is because when the concentration of Laminin-521 is lower than about 4.5 µg/ml, there is a possibility that functions as an adhesion molecule cannot be sufficiently exerted. Furthermore, when the concentration of commercially available Laminin-521 is taken into consideration, since the treatment becomes complex and the cost increases at a concentration greater than 100 µg/ml, the concentration is preferably 100 µg/ml or less.

In a case where a modified laminin is used as the laminin molecule 30, the modifying group may be, for example, a proliferation factor-binding molecule or a cell adhesion molecule. Similar action and effect to those of an unmodified laminin molecule can be exerted also in a case where such modified laminin is used. Alternatively, irrespective of the presence or absence of a modifying group, the fragment of the laminin molecule 30 may be used as the laminin molecule 30, or fragments or full lengths of a plurality of isofoams may be used by mixing, or may be used without mixing by being sequentially coated on the substrate 20. In a case where the fragment of the laminin molecule 30 is used as the laminin molecule 30, only a cell active site may be subjected to a peptide synthesis and used. Furthermore, the amount of the laminin molecule 30 used in this case may be an amount that corresponds to the molecular weight of the above-mentioned full-length laminin molecule 30.

In Case where Fragment of Laminin Molecule 30 is Used

In a case where the fragment of the laminin molecule 30 is used as the laminin molecule 30, for example, a variant of E8 region containing the cell adhesion site (integrin-binding site) of Domain I in a full-length laminin (represented by Laminin \*\*\*-E8) can be preferably used. Examples of such variant include Laminin-111-E8, Laminin-211-E8, Laminin-421-E8 and Laminin-521-E8. All of the molecular weights thereof is about one-fifth of the molecular weight of a full-length laminin.

In a case where, for example, a variant of E8 region of Laminin-511 (Laminin-511-E8) is used as the fragment of the laminin molecule 30, when the concentration of commercially available Laminin-511-E8 (iMatrix-511, Recombinant Laminin-511 E8-fragments: Nippi Inc.) is taken into consideration, it is preferable to conduct coating at a concentration of about 1.4 µg/ml or more and about 500 µg/ml or less to give an adhesion amount of 0.15 µg/cm$^2$ or more and 31.18 µg/cm$^2$ or less. By this way, the single layer structure of the culture cell can be maintained for 28 days or more. It is further preferable to conduct coating at a concentration of about 2.5 µg/ml or more and about 50 µg/ml or less to give an adhesion amount of 0.21 µg/cm$^2$ or more and 6.21 µg/cm$^2$ or less. In a case where the concentration is 1.3 µg/ml or less, the effect by coating is seen little. On the other hand, in a case where the concentration is greater than 500 µg/ml, it becomes difficult to adjust the coating solution.

As the fragment of the laminin molecule 30, a laminin peptide having cell adhesion activity can also be used besides the variant of E8 region or a fragment thereof. As such laminin peptide, for example, a YIGSR-containing peptide derived from Domain III of a β-chain, a PDSGR-containing peptide derived from Domain III of a β-chain, a RYVVLPR-containing peptide derived from Domain III of a β-chain, an RGD-containing peptide derived from Domain III of an α-chain, a KAFDITYVRLKF-containing peptide derived from Domain I of a γ-chain, an IKVAV-containing peptide derived from Domain I of an α-chain, an LRE-containing peptide derived from Domain I of a β-chain, and the like can be preferably used. The size of the fragment of the laminin molecule 30 is not specifically limited. In a case where a laminin peptide is used, it is sufficient to appropriately select the coating concentration in the range of about 0.5 to about 500 µg/ml.

As the laminin molecule 30, plural fragments of the laminin molecule 30 may be mixed and used, or the fragments of the laminin molecule 30 and a full-length laminin may be mixed and used, or the fragments of the laminin molecule 30 and other adhesion proteins such as gelatin, Collagen I, Collagen IV and Matrigel may be mixed and used.

Culture Cells 40

The culture cells 40 adhere to the substrate 20 via the laminin molecule 30 or the fragment thereof. In order to be used for the cell support composite 10, it is necessary that the culture cells 40 express a transporter 42 at the side of the apical membrane of the cell and a transporter 44 at the side of the basement membrane of the cell in a case where the culture cells 40 are immobilized on the substrate 20 via the laminin molecule 30 or the fragment thereof (FIG. 2).

The kind of the culture cells 40 is not specifically limited, and is preferably, for example, human renal tubule epithelial cells or renal tubule epithelial-like cells derived from human iPS cells or ES cells. Specifically, renal tubule epithelial cells that can be collected and separated from kidneys, and renal tubule epithelial-like cells obtained by inducing differentiation or transfecting from iPS cells or ES cells are envisaged. As the renal tubule epithelial-like cells, cells from a proximal tubule are mainly envisaged, but the renal tubule epithelial-like cells may be not only cells from a proximal tubule but also epithelial cells from a distal tubule, or epithelial cells from a collecting tubule. Alternatively, instead of the renal tubule epithelial cells, immortalized cells of renal tubule cells, and established cells (HK-2 cells), may be used, or cells obtained by transfecting these cells may be used for expressing proteins such as specific transporters. Alternatively, instead of human renal tubule epithelial cells, renal tubule cells derived from other animal species (MDCK cells, LLC-PK1 cells, JTC-12 cells) may also be used.

Culture Medium and the Like

As a culture medium for culturing the culture cells 40, a REGM (Lonza) can be preferably used. Instead of this culture medium, culture media for culturing renal tubule cells such as EpiCM (ScienCell) and Keratinocyte SFM (Life Technologies) can also be used. For the other materials, materials that have been used in conventional cell support composites can be preferably used.

Production Method

Secondly, the method for producing a cell support composite 10 is explained. The method for producing the cell support composite 10 includes: Step 1 for coating at least a part of a substrate 20 formed of an artificial material with a laminin molecule 30 or a fragment thereof; Step 2 for seeding a culture cells 40 onto the laminin molecule 30 or the fragment thereof that has adhered to the substrate 20; and Step 3 for culturing the culture cells 40 to form a single layer structure of the culture cells 40. "At least a part of the substrate 20" as referred to herein is as mentioned above.

It is preferable that the laminin molecule 30 for the coating in Step 1 is selected from one or more of Laminin-111, Laminin-211, Laminin-221, Laminin-311, Laminin-332, Laminin-421, Laminin-511 and Laminin-521, or fragments thereof. It is more preferable that the laminin molecule 30 is selected from one or more of Laminin-311, Laminin-511 and Laminin-521, or fragments thereof. As the fragment of the laminin molecule 30, for example, Laminin-511-E8 can be preferably used. The preferable concentrations for these laminin molecules 30 are as mentioned above.

In Step 2, the cell is seeded by a general method. The cell density for the seeding is preferably about $1.0 \times 10^5$ to about $1.0 \times 10^8$ cells/ml. When the laminin molecule 30 or the fragment thereof is appropriately selected, the culture cells 40 proliferate until confluent and maintain a confluent state. Therefore, in the production of the cell support composite 10, the number of cells to be seeded is not a significant limitation.

The culturing conditions in Step 3 are, for example, 37° C. and 5% $CO_2$ using an REGM (Lonza) as a culture medium. It is preferable to culture the culture cells 40 for about 5 days or more until the culture cells 40 become confluent. In addition, it is preferable to periodically replace the culture medium. For example, the culture medium is replaced every 2 days.

Action

When the culture cells 40, which function as renal tubule cells, have a single layer epithelial structure, the transfer of a useful substance 50 via a transporter 42 at the side of the apical membrane of each cell and a transporter 44 at the side of the basement membrane of each cell occurs, and the re-absorption of the useful substance 50 via the substrate 20 is promoted (FIG. 2).

Device

FIGS. 3A to 3C are drawings each showing a part of the structure of a device using the cell support composite in an embodiment. FIG. 3A is a drawing showing a part of the structure of a device using a Transwell as a substrate. FIG. 3B is a drawing showing a part of the structure of a dialyzer using a hollow fiber membrane as a substrate. FIG. 3C is a drawing showing a part of a device using a petri dish, a well plate, a fine flow path, a microcarrier or a hollow fiber membrane as a substrate.

In the device using a Transwell in FIG. 3A, by flowing a liquid on the side on which the culture cells 40 are disposed, and by using the mechanism shown in FIG. 2, a useful substance 50 in this liquid is transferred to the opposite side of the artificial membrane. This dialyzer can be used as a drug evaluation module in which the functions of the cell and the ingestion and ejection of a drug are investigated at a minute liquid amount.

In the dialyzer using a hollow fiber membrane in FIG. 3B, by flowing a liquid in the lumen of the hollow fiber membrane, and by using the mechanism shown in FIG. 2, a useful substance 50 in this liquid is transferred out of the lumen. This dialyzer can be used as a bioartificial renal module for collecting a useful substance from blood plasma components filtered by a blood filtering device.

In the devices using a petri dish, a well plate, a fine flow path, a microcarrier and hollow particles device in FIG. 3C, by flowing a minute amount of liquid on the side on which the culture cells 40 are disposed, the ingestion of the useful substance 50 by the cell can be confirmed. These devices can be utilized as modules for evaluating pharmacokinetics and medicinal effect in which the functions of the cell and the ingestion and ejection of a drug are investigated at a minute liquid amount.

The device includes, in addition to one or more of these structures, a cartridge for housing these structures inside. The material for the cartridge may be prepared by the same material as that of a conventional blood plasma filtration device. It is preferable that the shape of the cartridge is a preferable form depending on use. In a case where the device is used for dialysis, the shape of the cartridge is preferably a shape of a dialyzer, and in a case where the device is used as a drug evaluation module, the shape of the cartridge is preferably a shape of a Transwell or a shape of a fine flow path.

According to this embodiment, a confluent single layer epithelial structure of a culture cell can be formed on a substrate without observation under a microscope. As a result, a cell support composite in which the stability of the single layer epithelial structure has been improved can be provided. Furthermore, formation of pores in the single layer epithelial structure of the cell support composite can be prevented.

Specifically, in a case where a fragment of a laminin molecule is used, there is an advantage that more stable coating can be conducted as compared to a case where a full-length laminin molecule is used, since the fragment of a laminin molecule has a smaller molecular weight than that of the full-length laminin molecule. Furthermore, there is an advantage that fine regions are easily coated. Furthermore, since aggregation of laminin molecules hardly occurs, the formation of coating plaques during coating is reduced. Therefore, the inhomogeneity of the cell layer and the inhomogeneity of formation of a single layer of the cell can be prevented. Furthermore, by using a fragment of a laminin molecule, it becomes possible to coat the laminin molecule at a high concentration and a high density. Furthermore, since the production efficiency and purification efficiency increase at a lower molecular weight in a recombinant protein, the yield of the laminin molecule can be increased and the cost can further be decreased.

EXAMPLES

In Case where Substrate is Petri Dish (Well Plate): Screening of Laminin

A 96-well plate (made of polystyrene: CELLSTAR, Greiner Bio-one) as a substrate was coated with a laminin screening kit (LAM screen, Biolamina). The laminins used were Laminin-111, Laminin-211, Laminin-332, Laminin-421, Laminin-511 and Laminin-521. As a comparative example, cells were cultured without coating with a laminin (No coating). Furthermore, Laminin-411 was used as a comparative example. In the coating with the laminin, a laminin solution diluted to 10 µg/ml was added to wells and allowed to stand still at 4° C. overnight. 140 µl ($1.4 \times 10^4$ cells) of human proximal tubule cells (Lonza) ($1.0 \times 10^5$ cells/ml) were seeded, and cultured under conditions of 37° C. and 5% $CO_2$ by using an REGM (Lonza) as a culture medium. The culture medium was replaced every 2 days. The microscopic images (×10) after 1, 8 and 20 days had passed after the seeding are shown in FIG. 4.

The coating of the adhesion molecule was conducted by a method in which a coating solution containing an adhesion molecule is allowed to stand still at 4° C. overnight and conducting coating (overnight: a part of the adhesion molecule is coated), and a method in which a coating solution containing an adhesion molecule is allowed to stand still at 4° C. until the solution is completely dried (air drying: the whole amount of the adhesion molecule is coated).

Figure 4:
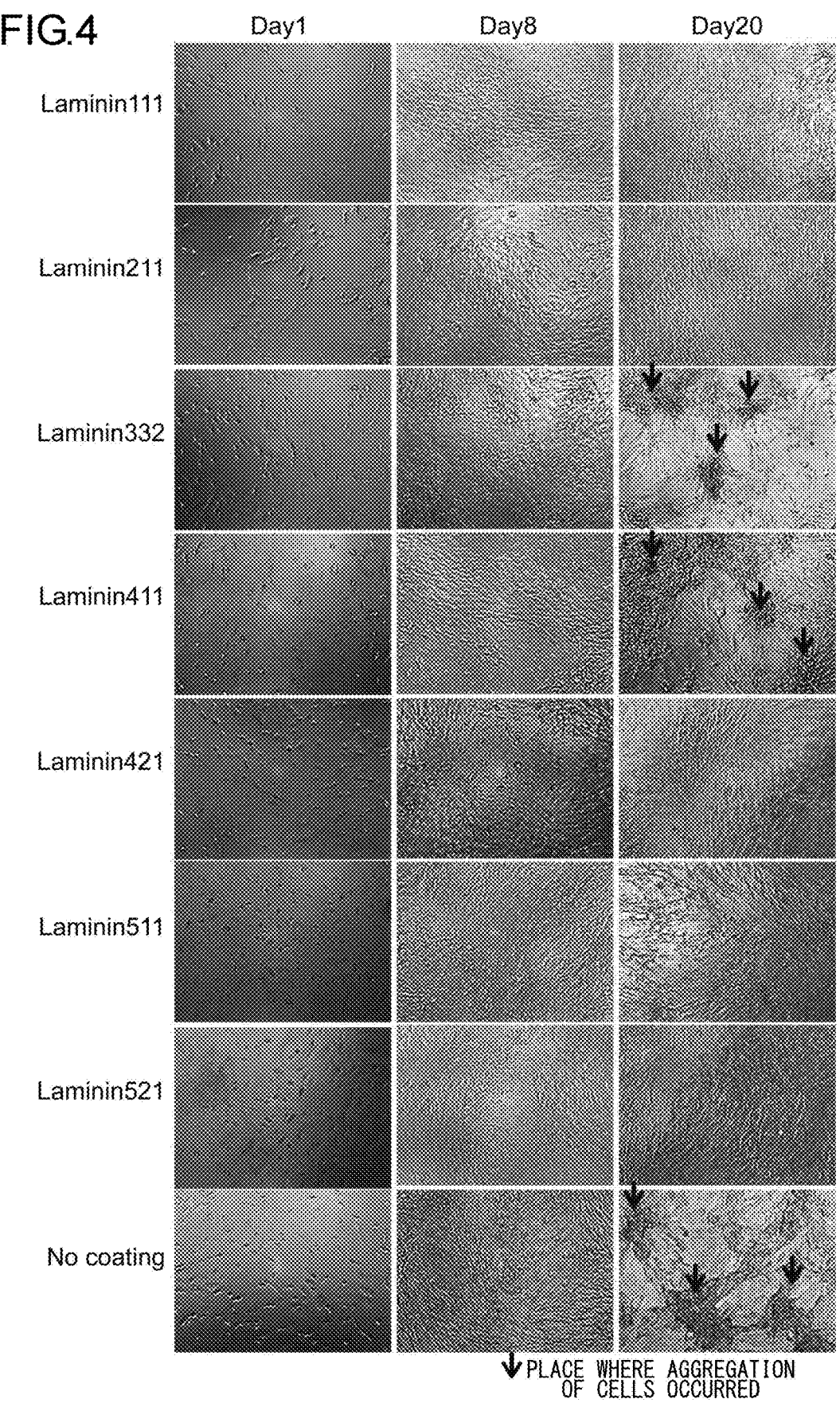
FIG. 4 is a drawing showing the proliferation state of cells over time in a case where the isofoam of a laminin for coating a petri dish is changed.

FIG. 4 is a drawing showing the proliferation state of cells over time in a case where the isofoam of a laminin for coating a petri dish is changed. In a case where the cells were cultured with no coating, the cells started to aggregate at more than about 1 week of culturing, and multilayering of the cells was confirmed (arrow in FIG. 4). Furthermore, in the cases where human proximal tubule epithelial cells were cultured by coating with Laminin-332 or Laminin-411, multilayering of the cells was confirmed up to the culturing for about 20 days (arrows in FIG. 4). On the other hand, it was confirmed that, in the cases where coating was conducted by using Laminin-111, Laminin-211, Laminin-421, Laminin-511 or Laminin-521, a single layer was able to be maintained without being aggregated even after 20 days (FIG. 4). For Laminin-332, when the concentration is increased, a single layer can be maintained up to at least day 24. This point is mentioned below by using FIGS. 6A to 6K.

In Case where Substrate is Petri Dish (Well Plate): Consideration of Coating Concentration 1

96-well plates (made of polystyrene: CELLSTAR, Greiner Bio-one) were coated with a Laminin-521 solution (Biolamina) adjusted to 100, 10, 5, 2, 1 and 0.1 µg/ml, and allowed to stand still at 4° C. overnight. As a comparative example, an experiment in which Laminin-521, which is an adhesion molecule, was not used was also conducted (Control). 140 µl ($1.4 \times 10^4$ cells) of $1.0 \times 10^5$ cells/ml of human proximal tubule cells (Lonza) were seeded, and cultured by using an REGM (Lonza) as a culture medium under conditions of 37° C. and 5% $CO_2$. The culture medium was replaced every 2 days. The microscopic images (×10) after 1 and 12 days had passed after the seeding are shown in FIG. 5.

Figure 5:
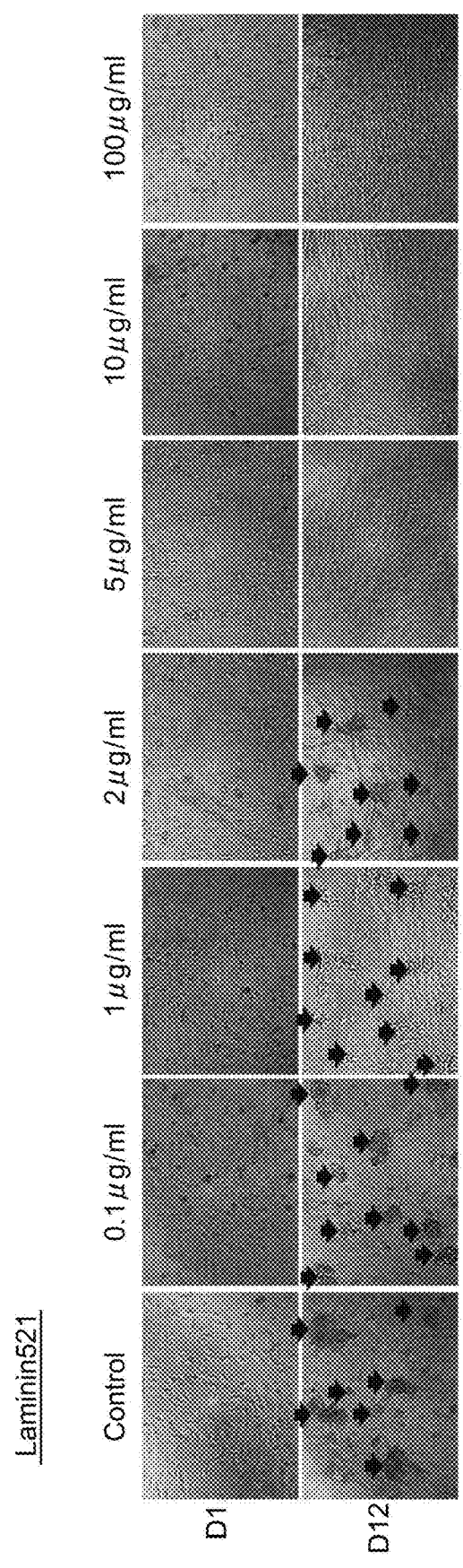
FIG. 5 is a drawing showing the proliferation state of cells over time in a case where the concentration of Laminin-521 for coating a petri dish is changed.

FIG. 5 is a drawing showing the proliferation state of cells over time in the case where the concentration of Laminin-521 for coating a petri dish was changed. From FIG. 5, after 12 days had passed after the seeding, aggregation of the cells were observed in Control (no Laminin-521), 0.1 µg/ml, 1 µg/ml and 2 µg/ml. It was clarified from this fact that the lower limit value of the concentration of Laminin-521 is preferably greater than 2 µg/ml, more preferably 3 µg/ml or more, the most preferably 5 µg/ml or more. On the other hand, regarding the upper limit value, it was clarified that Laminin-521 stably functions even at 100 µg/ml, which is a neat liquid of commercially available Laminin-521.

In Case where Substrate is Petri Dish (Well Plate): Consideration of Coating Concentration 2

Secondly, the coating concentration of the laminin molecule was considered for more laminin molecules (Laminin-111, 211, 221, 311, 332, 411, 421, 511 and 521) by labeling the concentration more minutely, and extending the number of days of culturing. The conditions were preset more minutely also for Laminin-521. As comparative examples, Synthemax and Poly-L-lysine were added.

24-well plates (made of polystyrene: CELLSTAR, Greiner Bio-one) were coated with a laminin screening kit (LAM screen, Biolamina). The coating was conducted by adding each of laminin solutions diluted to 100, 20, 10, 8.0, 6.0, 5.0, 4.0, 3.0, 2.0, 1.0, 0.5 and 0.1 µg/ml with PBS (+) to the wells, and allowing to stand still at 4° C. overnight. Before the seeding of the cells, the laminin solution was aspirated, and $1.0 \times 10^5$ cells of human proximal tubule cells (Lonza) were seeded and cultured by using an REGM (Lonza) as a culture medium under conditions of 37° C. and 5% $CO_2$. The culture medium was replaced every 2 days. The states of culturing after 1, 5, 7, 9, 12, 15, 18, 24 and 28 days had passed after the seeding are shown in FIGS. 6A to 6K.

As a comparative example, Synthemax was used. A 24-well plate (made of polystyrene: CELLSTAR, Greiner Bio-one) was coated with Synthemax (Corning). Each of the Synthemax solutions diluted to 100,000, 5,000, 3,000, 2,000, 1,000, 500, 100, 75, 50, 25, 10 and 5 µg/ml with an REGM were added to the wells, and allowed to stand still at room temperature. After 2 hours had passed, the Synthemax solution was aspirated and dried at room temperature for 2 hours. $1.0 \times 10^5$ cells of human proximal tubule cells (Lonza) were seeded and cultured by using an REGM (Lonza) as a culture medium under conditions of 37° C. and 5% $CO_2$. The culture medium was replaced every 2 days. The states of culturing after 1, 5, 7, 9, 12, 15, 18, 24 and 28 days had passed after the seeding are shown (FIGS. 6A to 6K).

Poly-L-lysine was also used as a comparative example. A 24-well plate (made of polystyrene: CELLSTAR, Greiner Bio-one) was coated with Poly-L-lysine (ScienCell). The coating was conducted by adding each of Poly-L-lysine solutions diluted to 100000, 5000, 3000, 2000, 1000, 500, 100, 75, 50, 25, 10, 5 µg/ml with PBS (−) to wells, and allowing to stand still at room temperature. After 2 hours had passed, the Poly-L-lysine solution was aspirated and dried at room temperature for 2 hours. Human proximal tubule cells (Lonza) ($1.0 \times 10^5$ cells) were seeded thereon and cultured by using an REGM (Lonza) as a culture medium under conditions of 7° C. and 5% $CO_2$. The culture medium was replaced every 2 days. The states of culturing after 1, 5, 7, 9, 12, 15, 18, 24 and 28 days had passed after the seeding are shown (FIGS. 6A to 6K).

Measurement of Mass of Adhesion Molecule in Case where Full-Length Laminin Molecule is Used A petri dish was coated with an adhesion molecule by the above-mentioned technology, and washed once with PBS (−). An M-PER Mammalian Protein Extraction Reagent (Thermo SCIENTIFIC), which is a protein solubilizing agent, was added thereto, and the adhesion molecule was peeled and collected from the surface of the petri dish by pipetting. The adhesion molecule was labeled with FITC by a 2-D Quant Kit (GE Healthcare) or a FluoReporter FITC protein Labeling Kit (invitrogen) and quantified (FIGS. 6A to 6K). For the quantification of the adhesion molecule, a wallac 1420ARVO MX/LIGHT (Perkin Elmer) was used.

FIGS. 6A to 6K are drawings showing the proliferation states of the cells over time in cases where the concentration of an adhesion molecule for coating a petri dish is changed. FIG. 6A is a drawing showing a result of use of Synthemax as a comparative example. FIG. 6B is a drawing showing a result of use of Poly-L-lysine as a comparative example. FIG. 6C is a drawing showing a result of use of Laminin-111 as an example. FIG. 6D is a drawing showing a result of use of Laminin-211 as an example. FIG. 6E is a drawing showing a result of use of Laminin-221 as an example. FIG. 6F is a drawing showing a result of use of Laminin-311 as an example. FIG. 6G is a drawing showing a result of use of Laminin-332 as an example. FIG. 6H is a drawing showing a result of use of Laminin-411 as an example. FIG. 6I is a drawing showing a result of use of Laminin-421 as an example. FIG. 6J is a drawing showing a result of use of Laminin-511 as an example. FIG. 6K is a drawing showing a result of use of Laminin-521 as an example.

In the tables, "Maximum Adhesion Amount (Air dried)" refers to the molecular amount of the adhered laminin molecule measured after allowing the coating solution to stand still at 4° C. until the substrate is coated with the laminin molecule by complete vaporization of the coating solution. In this case, since the substrate is coated with all of the laminin molecules contained in the coating solution, the adhesion molecular amount is equal to the whole amount of the laminin molecules contained in the coating solution before drying. On the other hand, "Adhesion Amount (overnight)" refers to the adhesion molecular amount after coating by allowing a coating solution containing the adhesion molecule to stand still at 4° C. overnight. In this case, an adhesion molecular amount corresponding to a part of the laminin molecules that have been actually used for the coating in the adhesion molecules is measured. Furthermore, "○" indicates that the pores of the single layer epithelial structure of the cell support composite are clogged by the proliferation of the cells and the single layer epithelial structure of the cells is maintained. The "tendency of aggregation is observed" in "Δ" refers to a case where pores have not been formed but cells have been partially stacked.

From FIG. 6A, even the concentration was adjusted to any concentration, the single layer structure of the culture cells was not able to be maintained over 7 days in Synthemax. Similarly, from FIG. 6B, even the concentration was adjusted to any concentration, the single layer structure of the culture cells was not able to be maintained over 7 days in Poly-L-lysine.

From FIG. 6C, in the case of Laminin-111, when coating was conducted at a concentration of 3.0 μg/ml or more to give an adhesion amount of about 0.15 μg/cm$^2$ or more, the single layer structure of the culture cells was able to be maintained for about 15 days or more. When the coating was conducted at a concentration of 4.0 μg/ml or more to give an adhesion amount of about 0.19 μg/cm$^2$ or more, the single layer structure of the culture cells was able to be maintained for 28 days or more. When the concentration of Laminin-111 is lower than 3.0 μg/ml, there is a possibility that the function as an adhesion molecule cannot be sufficiently exerted. Alternatively, when the concentration of commercially available Laminin-111 is taken into consideration, the treatment becomes complex at a concentration greater than 100 μg/ml. Furthermore, a large cost is required.

From FIG. 6D, in the case of Laminin-211, when the coating was conducted at a concentration of greater than 8.0 μg/ml to give an adhesion amount of greater than about 0.45 μg/cm$^2$, a single layer structure of the culture cells was able to be maintained for about 15 days or more. When the coating was conducted at a concentration of 10 μg/ml or more to give an adhesion amount of about 0.52 μg/cm$^2$ or more, a single layer structure of the culture cells was able to be maintained for 28 days or more. When the concentration of Laminin-211 becomes 8.0 μg/ml or less, there is a possibility that a function as an adhesion molecule cannot be sufficiently exerted. Furthermore, when the concentration of commercially available Laminin-211 is taken into consideration, the treatment becomes complex at a concentration greater than 100 μg/ml. Furthermore, a large cost is required.

From FIG. 6E, in the case of Laminin-221, when the coating was conducted at a concentration of greater than 8.0 μg/ml to give an adhesion amount of greater than about 0.30 μg/cm$^2$, a single layer structure of the culture cells was able to be maintained for about 15 days or more. When the coating was conducted at a concentration of 10 μg/ml or more to give an adhesion amount of about 0.34 μg/cm$^2$ or more, a single layer structure of the culture cells was able to be maintained for 18 days or more. When the concentration of Laminin-221 is 8.0 μg/ml or less, there is a possibility that a function as an adhesion molecule cannot be sufficiently exerted. Furthermore, when the concentration of commercially available commercially available Laminin-221 is taken into consideration, the treatment becomes complex at a concentration greater than 100 μg/ml. Furthermore, a large cost is required.

From FIG. 6F, in the case of Laminin-311, when the coating was conducted at a concentration of about 2.5 μg/ml or more to give an adhesion amount of about 0.10 μg/cm$^2$ or more, a single layer structure of the culture cells was able to be maintained for about 15 days or more. When the coating was conducted at a concentration of 4.0 μg/ml or more to give an adhesion amount of about 0.15 μg/cm$^2$ or more, a single layer structure of the culture cells was able to be maintained for 28 days or more. When the concentration of Laminin-311 was lower than about 2.5 μg/ml, there is a possibility that a function as an adhesion molecule cannot be sufficiently exerted. Furthermore, when the concentration of commercially available Laminin-311 is taken into consideration, the treatment becomes complex at a concentration greater than 100 μg/ml. Furthermore, a large cost is required.

From FIG. 6G, in the case of Laminin-332, when the coating was conducted at a concentration of 8.0 μg/ml or more, a single layer structure of the culture cells was able to be maintained for 15 days or more. When the coating was conducted at a concentration of 10 μg/ml or more, a single layer structure of the culture cells was able to be maintained for 18 days or more. When the concentration of Laminin-332 was lower than about 8.0 μg/ml, there is a possibility that a function as an adhesion molecule cannot be sufficiently exerted. Furthermore, when the concentration of commercially available commercially available Laminin-332 is taken into consideration, the treatment becomes complex at a concentration greater than 100 µg/ml. Furthermore, a large cost is required.

From FIG. 6H, in the case of Laminin-411, the culturing was not able to be conducted for a long time, without multilayering of the cells to a sufficient extent for practical use.

From FIG. 6I, in the case of Laminin-421, when the coating was conducted at a concentration of 5.0 µg/ml or more to give an adhesion amount of about 0.50 µg/cm$^2$ or more, a single layer structure of the culture cells was able to be maintained for 15 days or more. When the coating was conducted at a concentration of 6.0 µg/ml or more to give an adhesion amount of about 0.54 µg/cm$^2$ or more, a single layer structure of the culture cells was able to be maintained for 18 days or more. When the coating was conducted at a concentration of 10 µg/ml or more to give an adhesion amount of about 0.69 µg/cm$^2$ or more, a single layer structure of the culture cells was able to be maintained for 28 days or more. When the concentration of Laminin-421 is lower than about 0.50 µg/ml, there is a possibility that a function as an adhesion molecule cannot be sufficiently exerted.

Furthermore, when the concentration of commercially available Laminin-421 is taken into consideration, the treatment becomes complex at a concentration greater than 100 µg/ml. Furthermore, a large cost is required.

From FIG. 6J, in the case of Laminin-511, when the coating was conducted at a concentration of greater than about 8.0 µg/ml to give an adhesion amount of greater than about 0.30 µg/cm$^2$, a single layer structure of the culture cells was able to be maintained for about 15 days or more. When the coating was conducted at a concentration of 10 µg/ml or more to give an adhesion amount of about 0.32 µg/cm$^2$ or more, a single layer structure of the culture cells was able to be maintained for 18 days or more. Furthermore, when the concentration of Laminin-511 is about 8.0 µg/ml or less, there is a possibility that a function as an adhesion molecule cannot be sufficiently exerted. Furthermore, when the concentration of commercially available Laminin-511 is taken into consideration, the treatment becomes complex at a concentration greater than 100 µg/ml. Furthermore, a large cost is required.

From FIG. 6K, in the case of Laminin-521, when the coating was conducted at a concentration of about 4.5 µg/ml or more to give an adhesion amount of about 0.40 µg/cm$^2$ or more, a single layer structure of the culture cells was able to be maintained for about 15 days or more. When the coating was conducted at a concentration of 5.0 µg/ml or more to give an adhesion amount of about 0.44 µg/cm$^2$ or more, a single layer structure of the culture cells was able to be maintained for 28 days or more. When the concentration of Laminin-521 is lower than about 4.5 µg/ml, there is a possibility that a function as an adhesion molecule cannot be sufficiently exerted. Furthermore, when the concentration of commercially available Laminin-521 is taken into consideration, the treatment becomes complex at a concentration greater than 100 µg/ml. Furthermore, a large cost is required.

Observation of Layer Structure of Cells Using SEM

A PEPA-PES plane membrane was prepared from a PEPA-PES dissolved in NMP by a doctor blade process, the membrane was then installed in a 24-well plate (made of polystyrene: CELLSTAR, Greiner Bio-one), 300 µl of a Laminin-521 solution (Biolamina) adjusted to 10 µg/ml was added, and the mixture was allowed to stand still overnight at 4° C. Human proximal tubule epithelial cells (Lonza) (1.0×10$^5$ cells) were seeded on the well plate and cultured by using an REGM (Lonza) as a culture medium under conditions of 37° C. and 5% $CO_2$. The culture medium was replaced every 2 days. As a comparative example of an adhesion molecule, a gelatin solution adjusted to 0.1% (Cosmo Bio Co., Ltd.) was used by 300 µl each.

After the culturing for 3 weeks, the culture cells were washed with PBS (Nacalai Tesque), and immobilized by a 4% paraformaldehyde solution (Wako Pure Chemical Industries Ltd.) and a 2% osmium oxide solution (Wako Pure Chemical Industries Ltd.). Furthermore, dehydration was conducted by adding ethanol (Wako Pure Chemical Industries Ltd.) in the order of 70, 80, 90 and 100%, and the solvent was replaced with 100% butanol (Wako Pure Chemical Industries Ltd.). The resultant was lyophilized and observed under an SEM. The SEM pictures (×500, ×2,000, ×10,000) are shown in FIG. 7.

Figure 7:
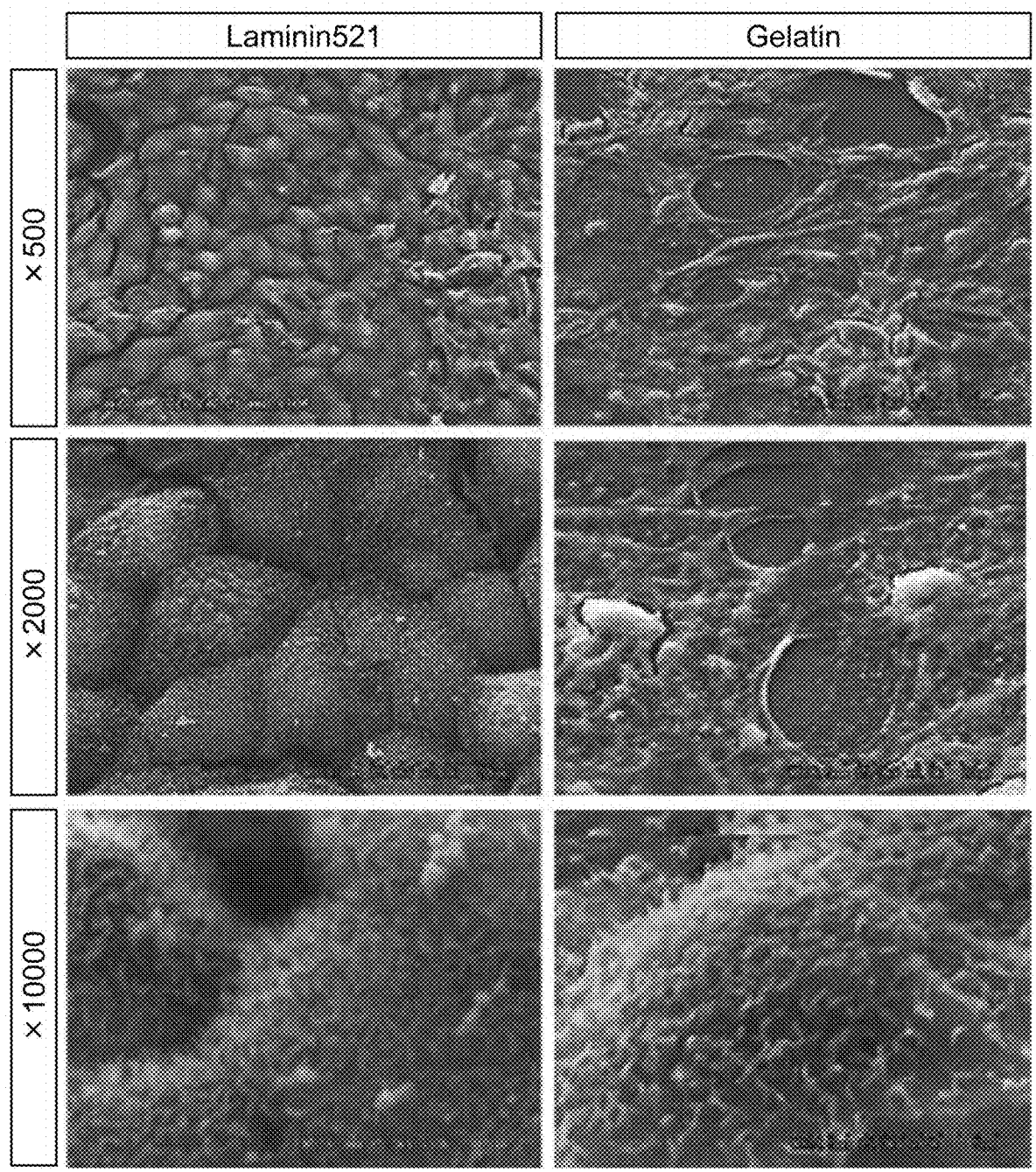
FIG. 7 shows microscopic photographs of the cell support composite of an example using Laminin-521 and the cell support composite of a comparative example using Gelatin.

FIG. 7 shows the microscopic photographs of the cell support composite of the example using Laminin-521 and the cell support composite of the comparative example using Gelatin. When proximal tubule epithelial cells were cultured on a PEPA hollow fiber membrane coated with gelatin, the cells were multilayered and flattened, and gaps were generated among the cells. On the other hand, when proximal tubule epithelial cells were cultured on a PEPA hollow fiber membrane coated with Laminin-521, cobblestone-like cells were distributed in the single layer, and thus the maintenance of the single layer epithelial structure was confirmed.

Furthermore, when a similar test was conducted by using a PES membrane as a substrate, maintenance of a single layer epithelial structure was similarly confirmed in Laminin-521, whereas, in gelatin, the cells were multilayered and flattened, and gaps were generated among the cells. It was clarified from these facts that the substrate can be selected relatively freely as long as the laminin molecule as an adhesion molecule is appropriately selected.

In Case where Substrate is Hollow Fiber 1: EVOH Hollow Fiber Membrane Minimodule The inner cavity of a hollow fiber membrane minimodule of an ethylene vinyl alcohol copolymer (EVOH) (Evaflux 5A20, Kawasumi Laboratories, Inc.) was washed with 100% ethanol, coated with a Laminin-521 solution (Biolamina) adjusted to 10 µg/ml, and allowed to stand still at 4° C. overnight. As comparative examples of the adhesion molecule, a gelatin solution adjusted to 0.1% (Cosmo Bio Co., Ltd.) and a PBS containing no adhesion molecule (without coating) were used.

After washing with PBS, human proximal tubule cells (Lonza) adjusted to 1.0×10$^7$ cells/ml were seeded, and allowed to stand still at 37° C. After 3 hours had passed, the top and bottom of the minimodule were reversed, and human proximal tubule cells (Lonza) adjusted to 1.0×10$^7$ cells/ml were seeded again and allowed to stand still at 37° C. After 3 hours had passed, the minimodule was immersed in a container filled with a REGM (Lonza) as a culture medium, and cultured under conditions of 37° C. and 5% $CO_2$. The culture medium was replaced every 2 days. The microscopic images (×20) after 1 and 14 days had passed after the seeding are shown in FIG. 8.

Figure 8:
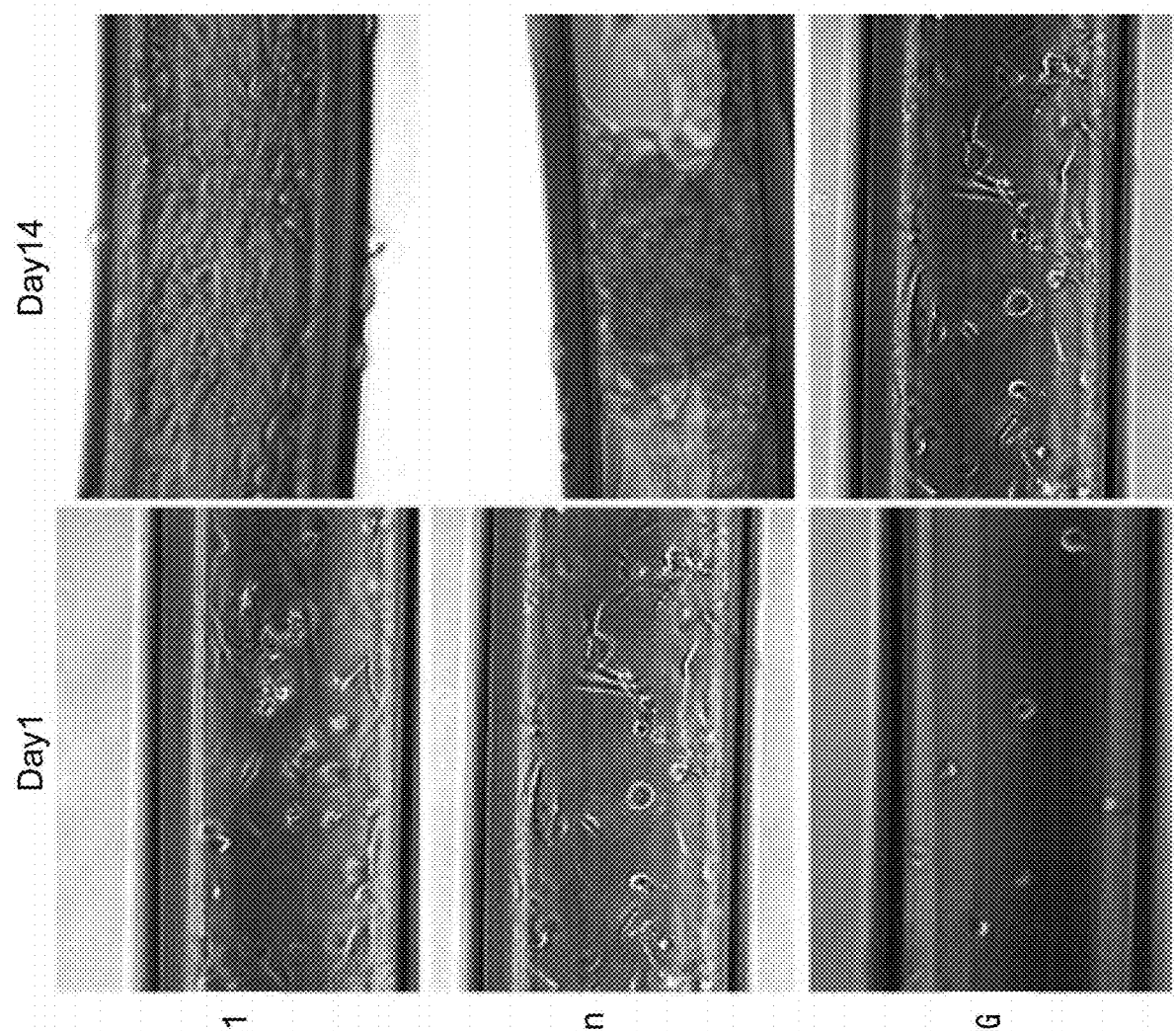
FIG. 8 shows microscopic photographs showing the proliferation states of the cells in an example using Laminin-521, in a comparative example using gelatin and in a comparative example having no coating in cases where an EVOH hollow fiber membrane is used as a substrate.

FIG. 8 shows microscopic photographs showing the proliferation states of the cells in an example using Laminin-521, in a comparative example using gelatin and in a comparative example having no coating in cases where a hollow fiber membrane is used as a substrate. When human proximal tubule epithelial cells were seeded on an EVOH hollow fiber membrane having no coating, the cells adhered little, and proliferated little even after 14 days had passed. When human proximal tubule epithelial cells were seeded on a gelatin-coated EVOH hollow fiber membrane, the multilayering of the cells progressed after 1 week of culturing, the multilayering of the cells progressed, and the multilayer became so large that the hollow fiber inner cavity was clogged on the 14th day of culturing. On the other hand, it was confirmed that a single layer structure was maintained for a long time when human proximal tubule cell were seeded on the EVOH hollow fiber membrane coated with Laminin-521.

In Case where Substrate is Polysulfone Hollow Fiber Membrane Minimodule

The inner cavity of a hollow fiber membrane minimodule of a polysulfone was washed with 100% ethanol, coated with a Laminin-521 solution (Biolamina) adjusted to 10 µg/ml, and allowed to stand still at 4° C. overnight. As a comparative example, a gelatin solution adjusted to 0.1% (Cosmo Bio Co., Ltd.) was used. After washing with PBS, human proximal tubule cells (Lonza) adjusted to $1.0 \times 10^7$ cells/ml were seeded, and allowed to stand still at 37° C. After 3 hours had passed, the top and bottom of the minimodule were reversed, and human proximal tubule cells (Lonza) adjusted to $1.0 \times 10^7$ cells/ml were seeded again and allowed to stand still at 37° C. After 3 hours had passed, the minimodule was immersed in a container filled with a REGM (Lonza) as a culture medium, and cultured under conditions of 37° C. and 5% $CO_2$. The culture medium was replaced every 2 days.

The cells were cultured for 3 weeks, then washed with PBS (Nacalai Tesque) and immobilized by using a 4% paraformaldehyde solution (Wako Pure Chemical Industries Ltd.). Thereafter dehydration was conducted by adding ethanol (Wako Pure Chemical Industries Ltd.) in the order of 70, 80, 90 and 100%, and the solvent was replaced with xylene (Wako Pure Chemical Industries Ltd.). The hollow fiber membrane was cut out of this minimodule, and subjected to an embedding treatment by using paraffin (Cosmo Bio Co., Ltd.). Using a Microtome (Yamato Kohki Industrial Co., Ltd.), a section having a thickness of 5 µm in the transverse cross-sectional direction was cut out of this embedded block. This section was attached to a slide glass (Matsunami Glass Ind., Ltd.), and subjected to deparaffinization treatment by immersing in xylene, 100, 90, 80 and 70% ethanol in this order to thereby put the cross-sectional surface of the artificial membrane hybridized with the culture cells into a stainable state. Secondly, the section was allowed to react with Hoechst 33342 (Dojindo Molecular Technologies, Inc.) diluted to 1,000-times for 1 hour to stain the nuclei of the cells. The cells were subjected to a dehydration treatment with ethanol and xylene, and encapsulated by using an encapsulating agent. The fluorescence microscopic images of these nuclear-stained cells are shown in FIG. 9.

Figure 9:
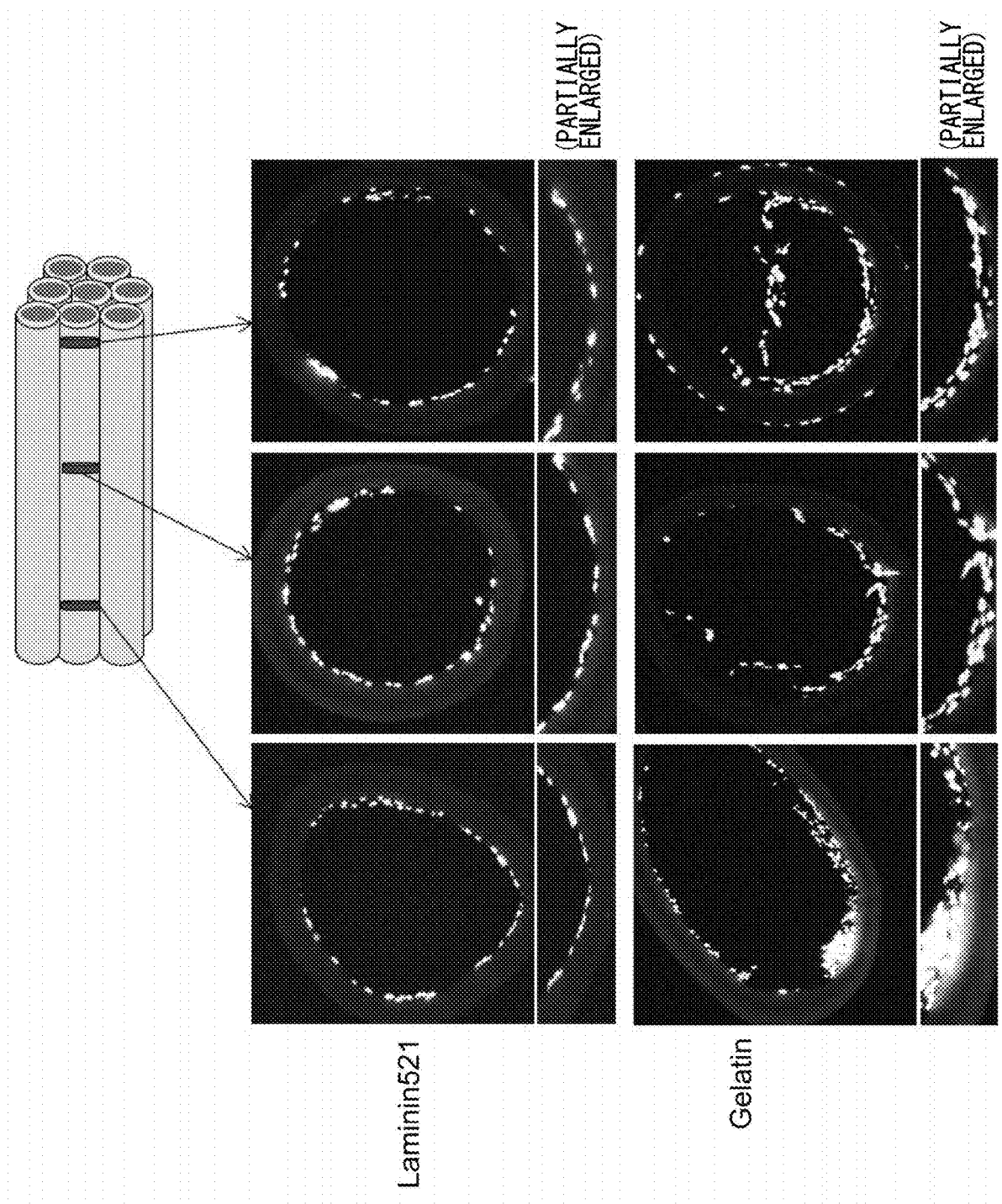
FIG. 9 shows fluorescence microscopic images of the nuclear-stained cells in an example using Laminin-521 and in a comparative example using gelatin in cases where a polysulfone hollow fiber membrane minimodule is used as a substrate.

FIG. 9 shows the fluorescence microscopic images of the nuclear-stained cells in an example using Laminin-521 and in a comparative example using gelatin in cases where a polysulfone hollow fiber membrane minimodule is used as a substrate. It was confirmed that, when the human proximal tubule epithelial cells were seeded on the gelatin-coated polysulfone hollow fiber membrane, the cells were multilayered. On the other hand, it was confirmed that, when the human proximal tubule epithelial cells were seeded on the Laminin-521-coated hollow fiber membrane, a single layer structure was maintained for a long time.

In Case where Substrate is PEPA Hollow Fiber Membrane Minimodule

The inner cavity of a PEPA hollow fiber membrane minimodule (Nikkiso Co., Ltd.) was washed with 100% ethanol, coated with a Laminin-521 solution (Biolamina) adjusted to 10 µg/ml, and allowed to stand still at 4° C. overnight. As a comparative example, a gelatin solution adjusted to 0.1% (Cosmo Bio Co., Ltd.) was used. Each minimodule was washed with PBS, and human proximal tubule cells (Lonza) adjusted to $1.0 \times 10^7$ cells/ml were seeded and the minimodule was allowed to stand still at 37° C. After 3 hours had passed, the top and bottom of the minimodule were reversed, and human proximal tubule cells (Lonza) adjusted to $1.0 \times 10^7$ cells/ml were seeded again, and the minimodule was allowed to stand still at 37° C. After 3 hours had passed, the minimodule was immersed in a container filled with a REGM (Lonza) as a culture medium, and cultured under conditions of 37° C. and 5% $CO_2$. The culture medium was replaced every 2 days.

The cells were cultured for 3 weeks, then washed with PBS (Nacalai Tesque) and immobilized by using a 4% paraformaldehyde solution (Wako Pure Chemical Industries Ltd.). Thereafter dehydration was conducted by adding ethanol (Wako Pure Chemical Industries Ltd.) in the order of 70, 80, 90 and 100%, and the solvent was replaced with xylene (Wako Pure Chemical Industries Ltd.). The hollow fiber membrane was cut out of this minimodule, and subjected to an embedding treatment by using paraffin (Cosmo Bio Co., Ltd.). Using a Microtome (Yamato Kohki Industrial Co., Ltd.), a section having a thickness of 5 µm in the transverse cross-sectional direction was cut out of this embedded block. This section was attached to a slide glass, and subjected to deparaffinization treatment by immersing in xylene, 100, 90, 80 and 70% ethanol in this order to thereby put the cross-sectional surface of the artificial membrane hybridized with the proximal tubule epithelial cells into a stainable state. Secondly, the section was allowed to react with Hoechst 33342 (Dojindo Molecular Technologies, Inc.) diluted to 1,000-times for 1 hour to stain the nuclei of the cells. The cells were subjected to a dehydration treatment with ethanol and xylene, and encapsulated by using an encapsulating agent. The fluorescence microscopic images of these nuclear-stained cells are shown in FIG. 10.

Figure 10:
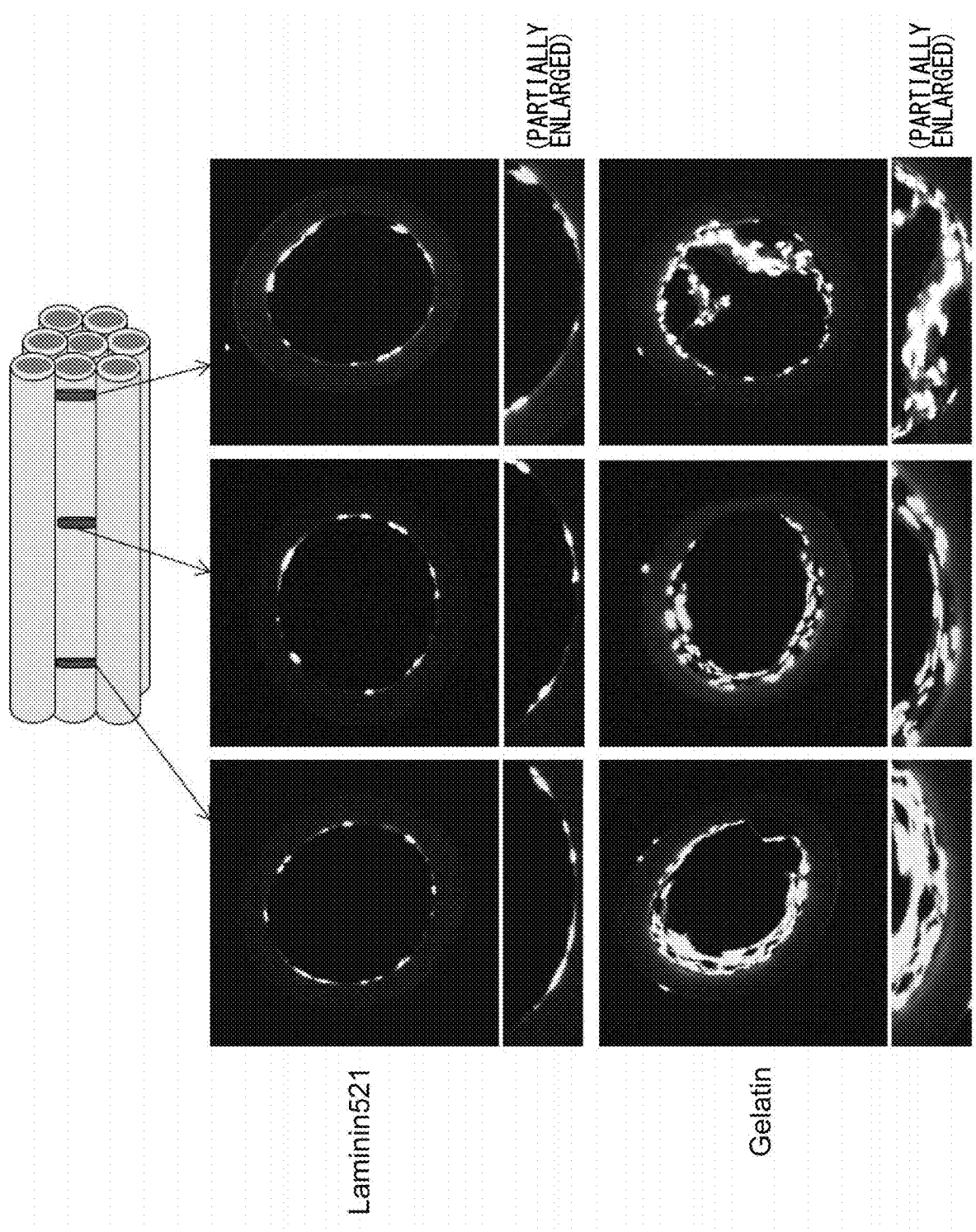
FIG. 10 shows fluorescence microscopic images of nuclear-stained cells in an example using Laminin-521 and in a comparative example using gelatin in cases where a PEPA hollow fiber membrane minimodule is used as a substrate.

FIG. 10 shows fluorescence microscopic images of nuclear-stained cells in an example using Laminin-521 and in a comparative example using gelatin in cases where a PEPA hollow fiber membrane minimodule is used as a substrate. It was confirmed that, when the human proximal tubule epithelial cells were seeded on the gelatin-coated PEPA hollow fiber membrane, the cells were multilayered. On the other hand, it was confirmed that, when the human proximal tubule epithelial cells were seeded on the Laminin-521-coated hollow fiber membrane, a single layer structure was maintained for a long time.

In Case of Transwell 1

Figure 11A:
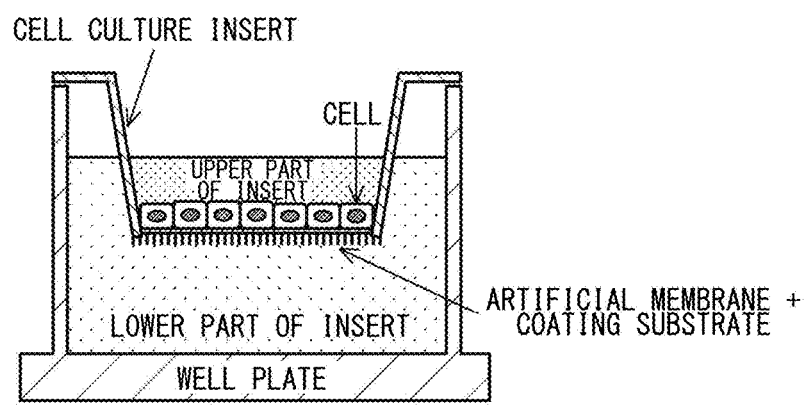
FIGS. 11A to 11C are drawings showing an example using Laminin-521 and a comparative example using gelatin where the substrate is immobilized on a Transwell.
Figure 11B:
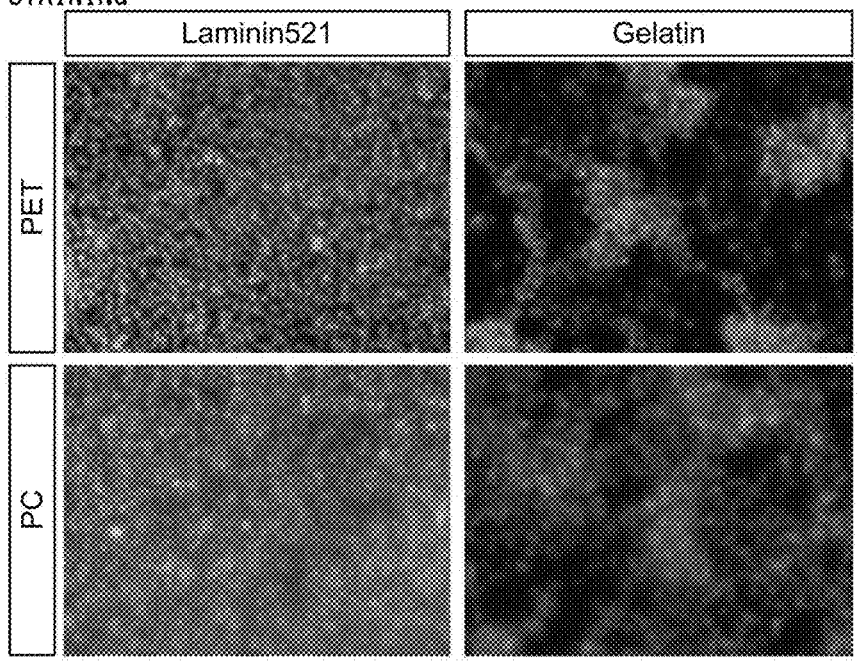
Figure 11C:
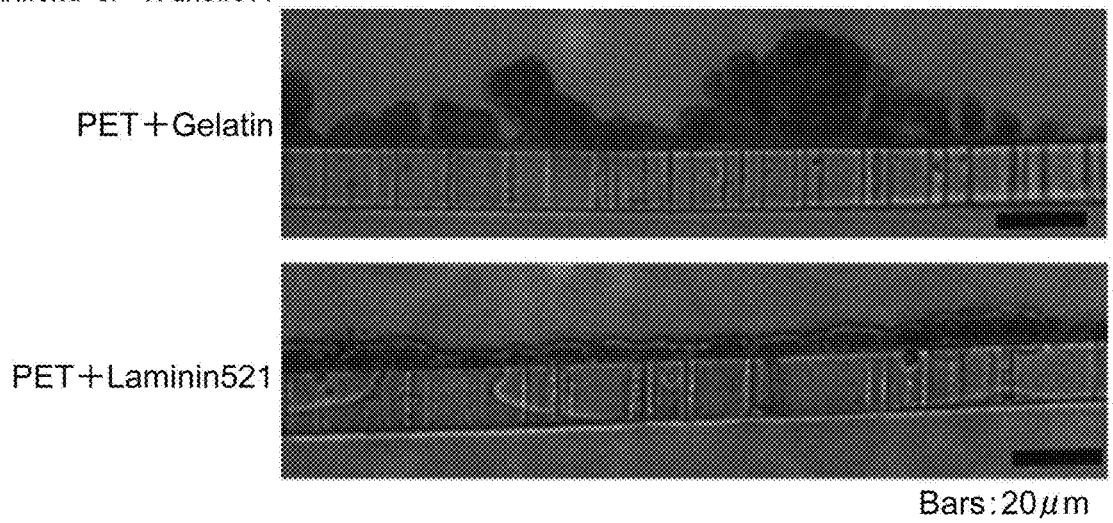

FIGS. 11A to 11C are drawings showing an example using Laminin-521 and a comparative example using gelatin where the substrate is immobilized on a Transwell. FIG. 11A is a schematic view of a Transwell seen from the side surface. The "artificial membrane+coating substrate" in FIG. 11A represents a substrate coated with Laminin-521. As shown in FIG. 11A, a Transwell cell culture insert (PC, PET; pore size 0.4 μm: Transwell (Corning)) was installed in a 24-well plate. Thereafter, 700 μl of PBS (Nacalai Tesque) was added to the lower part of the insert and 300 μl of a Laminin-521 solution (Biolamina) adjusted to 10 μg/ml was added to the upper part of the insert, and the insert was allowed to stand still at 4° C. overnight. As a comparative example, a gelatin solution adjusted to 0.1% (Cosmo Bio Co., Ltd.) was used. Secondly, 140 μl ($1.4 \times 10^4$ cells) of $1.0 \times 10^5$ cells/ml of human proximal tubule epithelial cells (Lonza) were seeded onto a substrate obtained by coating a Transwell (Corning) with Laminin-521, and cultured by an REGM (Lonza) under conditions of 37° C. and 5% $CO_2$. The culture medium was replaced every 2 days.

After the culturing for 3 weeks, the culture cells were washed with PBS (Nacalai Tesque), and immobilized by a 4% paraformaldehyde solution (Wako Pure Chemical Industries Ltd.). Secondly, the section was allowed to react with Hoechst 33342 (Dojindo Molecular Technologies, Inc.) diluted to 1,000-times for 1 hour to stain the nuclei of the cells. The fluorescence microscopic images of these nuclear-stained cells are shown in FIG. 11B.

Furthermore, dehydration was conducted by adding ethanol (Wako Pure Chemical Industries Ltd.) in the order of 70, 80, 90 and 100%, and the solvent was replaced with xylene (Wako Pure Chemical Industries Ltd.). The hollow fiber membrane was cut out of this minimodule, and subjected to an embedding treatment by using paraffin (Cosmo Bio Co., Ltd.). Using a Microtome (Yamato Kohki Industrial Co., Ltd.), a section having a thickness of 5 μm was cut out of this embedded block. This section was attached to a slide glass, and subjected to a deparaffinization treatment by immersing in xylene, 100, 90, 80 and 70% ethanol in this order to thereby put the cross-sectional surface of the artificial membrane hybridized with the proximal tubule epithelial cells into a stainable state. This artificial membrane was reacted with a Mayer's Hematoxylin Solution (Wako Pure Chemical Industries Ltd.), which is a cell nucleus-staining agent, and reacted with an Eosin Y Solution (Wako Pure Chemical Industries Ltd.), which is a cytoplasm staining agent. Furthermore, the cells were subjected to a dehydration treatment with ethanol and xylene, and encapsulated by using an encapsulating agent. The microscopic images of these HE-stained cells are shown in FIG. 11C.

FIG. 11B shows fluorescence microscopic images of nuclear-stained cells in an example using Laminin-521 and a comparative example using gelatin. FIG. 11C shows microscopic images in which the cells are HE-stained regarding the cross-sectional surface of the Transwell. When the human proximal tubule epithelial cells were cultured on an artificial membrane (a PC or PET membrane) as a substrate, in the case where the artificial membrane was coated with Laminin-521 as an example, the nuclei were homogeneously distributed on an artificial membrane, and the cells were distributed in a single layer (FIG. 11B). On the other hand, in the case where the artificial membrane was coated with gelatin as a comparative example, the nuclei were distributed in an aggregated manner on the artificial membrane, and the cells were overlapped (FIG. 11B). Furthermore, from the cross-sectional drawing of the Transwell, the human proximal tubule epithelial cells were overlapped on the gelatin-coated PET membrane, whereas the state of a single layer was maintained on the Laminin-521-coated PET membrane (FIG. 11C).

It was found from this result that, also in the cases where the PC or PET membrane was used as the substrate, the single layer structure of the human proximal tubule epithelial cells can be maintained for a long time by coating with Laminin-521.

In Case of Transwell 2: Consideration of Pore Size of Substrate

Transwell cell culture inserts (PC; pore size 0.4, 3.0, 5.0, 8.0 μm: Transwell (Corning)) were each installed in 24-well plates. Thereafter, 700 μl of PBS (Nacalai Tesque) was added to the lower part of each insert and 300 μl of a Laminin-521 solution (Biolamina) adjusted to 10 μg/ml was added to the upper part of each insert, and the insert was allowed to stand still at 4° C. overnight. As a comparative example, a gelatin solution adjusted to 0.1% (Cosmo Bio Co., Ltd.) was used. 140 μl ($1.4 \times 10^4$ cells) of $1.0 \times 10^5$ cells/ml of human proximal tubule epithelial cells (Lonza) were seeded onto a Transwell (Corning) coated with Laminin-521, and cultured by using an REGM (Lonza) under conditions of 37° C. and 5% $CO_2$ for 2 days. As a comparative example of the adhesion molecule, each 300 μl of a gelatin solution (Cosmo Bio Co., Ltd.) adjusted to 0.1% was used. After the culturing, the bottom part of the 24-well plate was observed under a microscope, and whether or not the cells had fallen from the artificial membrane was investigated.

As a result, in the cases where the pore size (PC) of the artificial membrane of the Transwell coated with Laminin-521 was 5.0 or 8.0 μm, the seeded cells passed through the membrane. However, in the case where the pore size was 5.0 μm, the cells were sometimes difficult to pass the membrane. On the other hand, in the cases where the pore size was 0.3 or 3.0 μm, the seeded cells did not pass through the membrane. Therefore, it was clarified that, in a case where the optional number of cells is seeded on an artificial membrane, it is preferable to use an artificial membrane having a pore size of lower than 5.0 μm. Furthermore, a similar tendency was indicated in the case where a similar test was conducted by using the gelatin-coated Transwell as a comparative example.

Consideration of Cell Epithelial Resistance Value in Case where Full-Length Laminin Molecule is Used Test method: 140 μl ($1.4 \times 10^4$ cells) of $1.0 \times 10^5$ cells/ml of human proximal tubule epithelial cells (Lonza) were seeded onto a Transwell (Corning) coated with Laminin-311, Laminin-511 or Laminin-521, and cultured by an REGM (Lonza) under conditions of 37° C. and 5% $CO_2$ for 28 days. The culture medium was replaced every 2 days. During the culturing, a transepithelial electro resistance value (TEER), which is an index of the barrier function of the cells, was measured by a Millicell ERS-2 (Millipore).

When the values of the electro resistances after the culturing for 28 days were compared (Laminin-111=1), the values were Laminin-211=0.8, Laminin-221=0.8, Laminin-311=1.3, Laminin-332=0.8, Laminin-411=0.9, Laminin-421=0.8, Laminin-511=1.1, and Laminin-521=1.2. Therefore, the laminin species that increased the barrier function of the cell layer more than Laminin-111 did were Laminin-311, Laminin-511 and Laminin-521.

In Case where Fragment of Laminin Molecule is Used: Consideration of Coating Concentration 1

24-well plates (made of polystyrene: CELLSTAR, Greiner Bio-one) were coated with iMatrix-511 (Laminin- 511-E8 solution: Nippi Inc.) adjusted to 500, 50, 2.5, 1.0, 0.5, 0.1 and 0 μg/ml. The coating was conducted by adding a laminin solution diluted to each of these concentrations with PBS (−) to the wells, and allowed to stand still at 4° C. overnight. $1.0 \times 10^5$ cells/ml of human proximal tubule cells (Lonza) were seeded onto the wells, and cultured by using an REGM (Lonza) as a culture medium under conditions of 37° C. and 5% $CO_2$. The culture medium was replaced every 2 days. The microscopic images (×10) after 15 days had passed after the seeding are shown.

Figure 12:
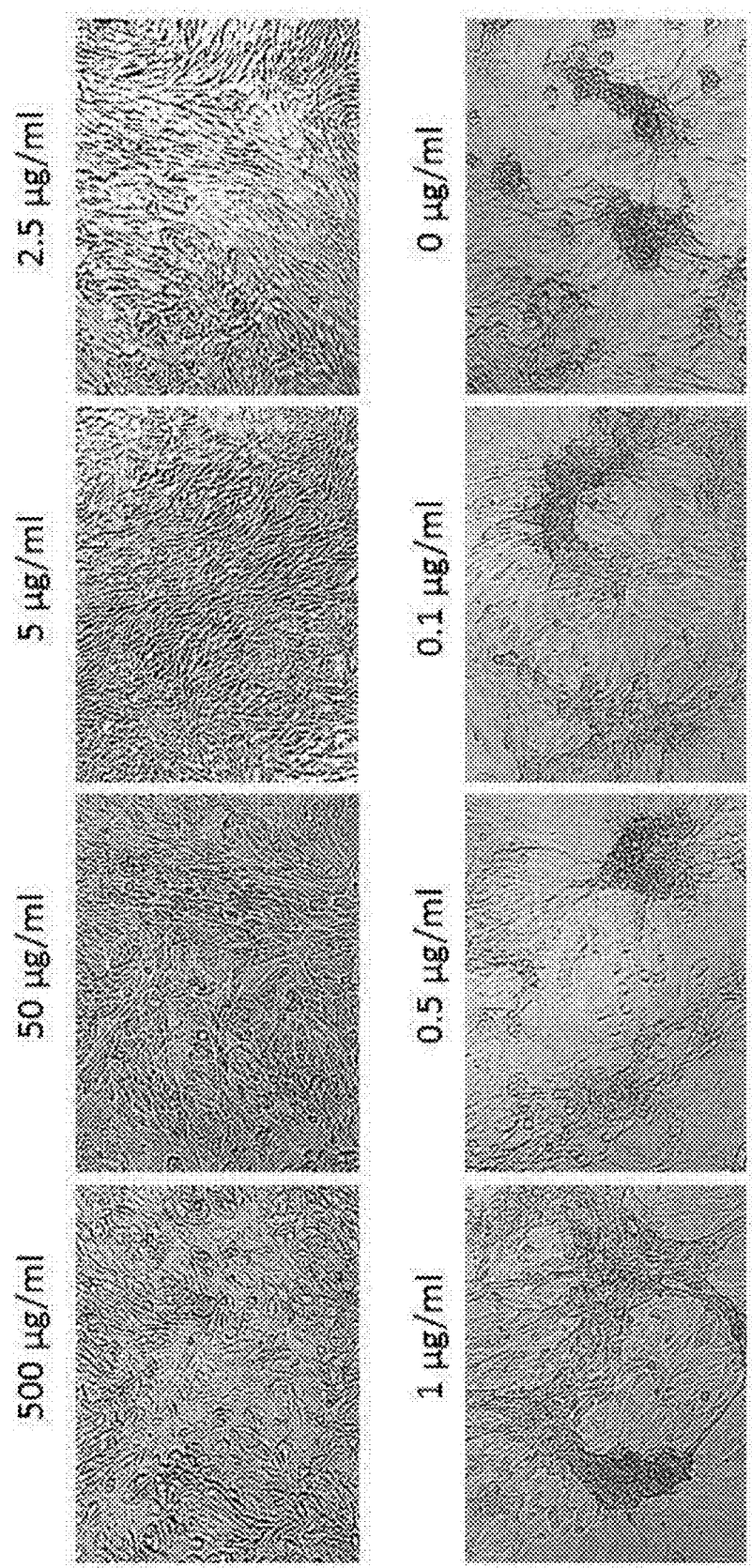
FIG. 12 is a drawing showing the proliferation state at 15 days after seeding in a case where the concentration of Laminin-511-E8, which is a fragment of the laminin molecule 30 for coating a petri dish, is changed.

FIG. 12 is a drawing showing the proliferation state at 15 days after the seeding in a case where the concentration of Laminin-511-E8, which is a fragment of the laminin molecule 30 for coating the petri dish, was changed. It was confirmed from FIG. 12 that the shape of the human proximal tubule cells changed from a single layer so as to form an aggregate at a coating concentration between 1 μg/ml and 2 μg/ml.

In Case where Variant of Laminin Molecule is Used: Consideration of Coating Concentration 2

Secondly, the proliferation states of the cells over time in cases where the concentration of 511-E8 were changed were confirmed in more detail. This consideration is different from the above-mentioned "Consideration of coating concentration 1" in that laminin solutions diluted to 500, 100, 50, 10, 5, 2.5, 1.7, 1.43, 1.25, 1.0, 0.5, 0 μg/ml were used for the coating with iMatrix-511 (Laminin-511-E8 solution: Nippi Inc.), and that microscopic images (×10) after 5, 9, 12, 15, 18 and 28 days had passed after the seeding were obtained.

Figure 13:
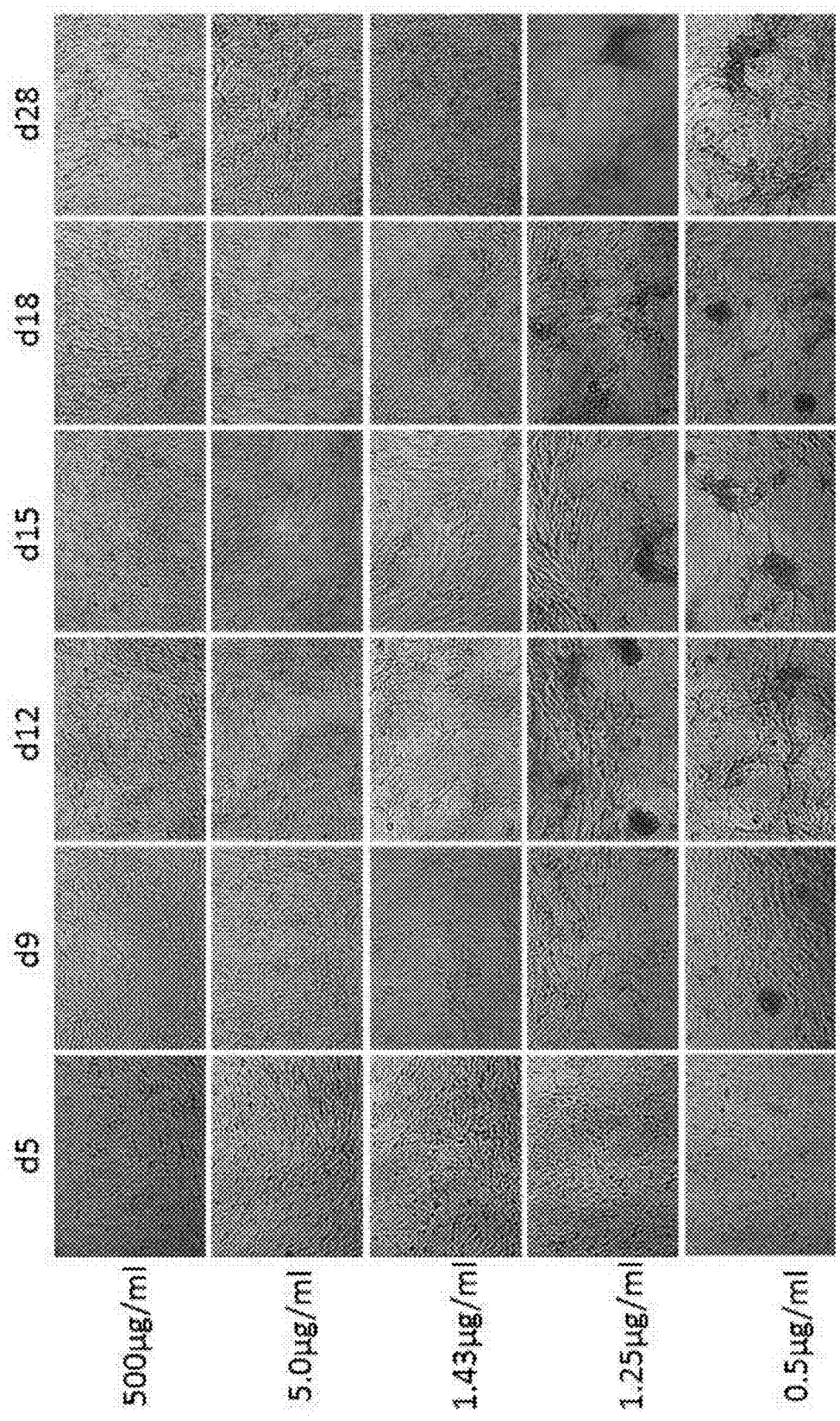
FIG. 13 is a drawing showing the changes over time in the forms of the cells in cases where the concentration of Laminin-511-E8, which is a fragment of the laminin molecule 30 for coating a petri dish, is changed.

FIG. 13 is a drawing showing the changes over time in the forms of the cells in cases where the concentration of Laminin-511-E8, which is a fragment of the laminin molecule 30 for coating the petri dish, was changed. It was confirmed from FIG. 13 that the shape of the human proximal tubule cells changed from a single layer so as to form an aggregate at a coating concentration between 1.25 μg/ml and 1.43 μg/ml.

In Case where Variant of Laminin Molecule is Used: Measurement of Mass of Adhesion Amount By a similar technology to that of the above-mentioned "Measurement of mass of adhesion molecule in full-length laminin molecule", the mass of the adhesion amount in a case where a fragment of a laminin molecule was used as a variant of the laminin molecule was measured. The shapes of the cells after 5, 7, 9, 12, 15, 18, 24 and 28 days had passed after the seeding and the adhesion amounts of Laminin-511-E8 are shown in FIG. 14.

FIG. 14 is a drawing showing the results of the measurements of the mass of the adhesion molecule and the changes over time of the proliferation state of the cell in cases where the concentration of Laminin-511-E8, which is a fragment of the laminin molecule 30 for coating the petri dish, was changed. In the cases where Laminin-511-E8 was coated at a concentration of about 1.4 μg/ml or more and about 500 μg/ml or less to give adhesion amounts of 0.15 μg/cm² or more and 31.18 μg/cm² or less, a single layer structure of the culture cells was able to be maintained for 28 days or more. In the cases where the concentration was 1.3 μg/ml or less, the effect by coating was observed little. On the other hand, in the cases where the concentration was greater than 500 μg/ml, the coating solution was difficult to be adjusted.

In Case where Variant of Laminin Molecule is Used: Consideration of Cell Epithelial Resistance Value Test method: 150 μl ($4.5 \times 10^4$ cells) of $3.0 \times 10^5$ cells/ml of human proximal tubule epithelial cells (Lonza) were seeded on a Transwell (Corning) coated with 1.5 μg/cm² of Laminin-511-E8 and 1.0 μg/cm² of Laminin-521, and cultured by an REGM (Lonza) under conditions of 37° C. and 5% $CO_2$. The culture medium was replaced every 2 days. During the culturing, a transepithelial electro resistance value (TEER), which is an index of the barrier function of the cells, was measured by a Millicell ERS-2 (Millipore).

Figure 15:
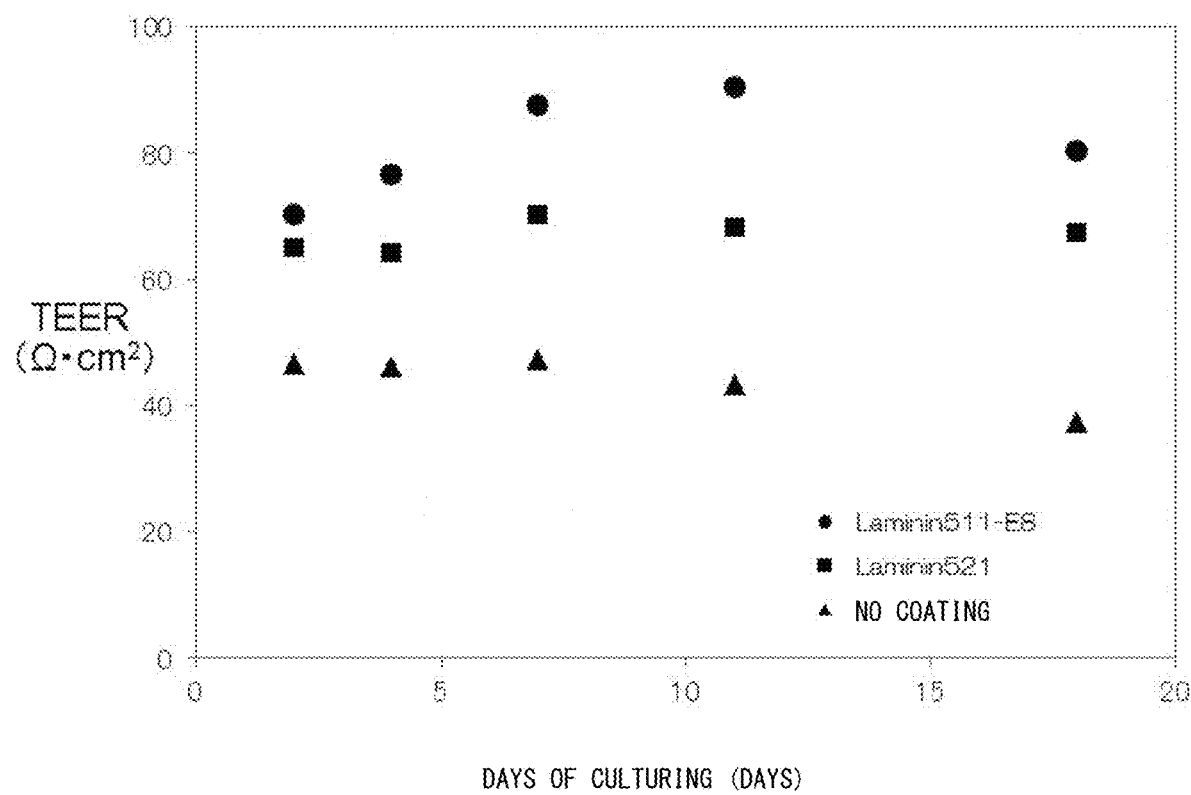
FIG. 15 is a drawing showing changes over time of the TEER values after 2, 4, 7, 11 and 18 days passed after seeding in cases where coating is conducted by using Laminin-511-E8 or Laminin-521.

FIG. 15 is a drawing showing changes over time of the TEER values after 2, 4, 7, 11 and 18 days passed after seeding in cases where coating was conducted by using Laminin-511-E8 and Laminin-521. It was confirmed from FIG. 15 that the TEER value increased when the human proximal tubule epithelial cells were seeded on the Transwell coated with Laminin-511-E8 and Laminin-521. It was confirmed from this fact that the cells having a high density adhered onto the Transwell. Furthermore, the TEER value tended to be higher in the coating with Laminin-511-E8 than that in the coating with Laminin-521. It is suggested from this fact that Laminin-511-E8 adhered at a higher density than Laminin-521 and the cells having a higher density than that of the cells in the case of Laminin-521 adhered to Laminin-511-E8 on the Transwell. A similar effect is expected also for other variants of E8 region of a laminin molecule such as Laminin-311-E8 and Laminin-521-E8.

The present invention has been explained above based on Examples. It is understood by persons skilled in the art that the present invention is not limited to the above-mentioned embodiment and can be designed and modified in various ways, and various modified examples are possible, and such modified examples are also in the scope of the present invention.

What is claimed is:

1. A cell support composite comprising:
   a substrate formed of an artificial material;
   a laminin molecule or a fragment thereof which adheres to at least a part of the substrate; and
   a monolayer of a renal tubule epithelial cell or a renal tubule epithelial-like cell which is a cultured cell attached to the substrate via the laminin molecule or the fragment thereof, wherein the monolayer of the renal tubule epithelial cell or the renal tubule epithelial-like cell is maintained for 15 days or more,
   wherein the laminin molecule or the fragment thereof is selected from any one of
   Laminin-111 or a fragment thereof that adheres to the substrate at an amount of 0.15 μg/cm² or more,
   Laminin-211 or a fragment thereof that adheres to the substrate at an amount of 0.52 μg/cm² or more,
   Laminin-221 or a fragment thereof that adheres to the substrate at an amount of 0.34 μg/cm²,
   Laminin-311 or a fragment thereof that adheres to the substrate at a maximum amount after air drying of 0.5 μg/cm² or more,
   Laminin-332 or a fragment thereof that adheres to the substrate at a maximum amount after air drying of 1.2 μg/cm² or more,
   Laminin-421 or a fragment thereof that adheres to the substrate at an amount of 0.50 μg/cm² or more,
   Laminin-511 or a fragment thereof that adheres to the substrate at an amount of 0.32 μg/cm² or more, a variant of E8 region of Laminin-511 that adheres to the substrate at an amount of 0.15 μg/cm² or more, and
Laminin-521 or a fragment thereof that adheres to the substrate at an amount of 0.44 μg/cm² or more.

2. The cell support composite according to claim 1, wherein the laminin 311 or the fragment thereof adheres to the substrate at an amount of 0.15 μg/cm² or more.

3. The cell support composite according to claim 1, wherein the cultured cell has formed a confluent single layer without being substantially multilayered.

4. A method for producing the cell support composite of claim 1, comprising:
    coating at least a part of a substrate formed of an artificial material with a laminin molecule or a fragment thereof;
    seeding a renal tubule epithelial cell or a renal tubule epithelial-like cell which is a cultured cell on the laminin molecule or the fragment thereof that has adhered to the substrate; and
    culturing the cultured cell to give a single layer structure of the cultured cell,
    wherein the coating with the laminin molecule or the fragment thereof comprises any one of:
    coating with Laminin-111 at a concentration of 3.0 mg/ml or more to give an adhesion amount of 0.15 mg/cm² or more;
    coating with Laminin-211 at a concentration of 10.0 mg/ml or more to give an adhesion amount of 0.52 mg/cm² or more;
    coating with Laminin-221 at a concentration of 10.0 mg/ml or more to give an adhesion amount of 0.34 mg/cm² or more;
    coating with Laminin-311 at a concentration of 3.0 mg/ml or more to give a maximum adhesion amount after air drying of 0.5 mg/cm² or more;
    coating with Laminin-332 at a concentration of 5.0 mg/ml or more to give a maximum adhesion amount after air drying of 1.2 mg/cm² or more;
    coating with Laminin-421 at a concentration of 5.0 mg/ml or more to give an adhesion amount of 0.50 mg/cm² or more;
    coating with Laminin-511 at a concentration of 10.0 mg/ml or more to give an adhesion amount of 0.32 mg/cm² or more;
    coating with a variant of E8 region of Laminin-511 at a concentration of 1.4 mg/ml or more to give an adhesion amount of 0.15 mg/cm² or more; and
    coating with Laminin-521 at a concentration of 5.0 mg/ml or more to give an adhesion amount of 0.44 mg/cm² or more.

5. The method for producing a cell support composite according to claim 4, wherein the coating with the laminin molecule or the fragment thereof comprises any one of:
    coating with Laminin-311 at a concentration of 4.0 mg/ml or more to give an adhesion amount of 0.15 mg/cm² or more;
    coating with Laminin-511 at a concentration of 10.0 mg/ml or more to give an adhesion amount of 0.32 mg/cm² or more;
    coating with a variant of E8 region of Laminin-511 at a concentration of 1.4 mg/ml or more to give an adhesion amount of 0.15 mg/cm² or more; and
    coating with Laminin-521 at a concentration of 5.0 mg/ml or more to give an adhesion amount of 0.44 mg/cm² or more.

6. The method for producing a cell support composite according to claim 4, wherein the cultured cell has formed a confluent single layer without being substantially multilayered.

* * * * *